(12) United States Patent
Fallin et al.

(10) Patent No.: US 7,572,275 B2
(45) Date of Patent: Aug. 11, 2009

(54) SYSTEM AND METHOD FOR ANCHORING SUTURE TO BONE

(75) Inventors: T. Wade Fallin, Hyde Park, UT (US); M. Mary Sinnott, Logan, UT (US)

(73) Assignee: Stryker Endoscopy, San Jose, CA (US)

( * ) Notice: Subject to any disclaimer, the term of this patent is extended or adjusted under 35 U.S.C. 154(b) by 899 days.

(21) Appl. No.: 11/008,006

(22) Filed: Dec. 8, 2004

(65) Prior Publication Data

US 2006/0122608 A1    Jun. 8, 2006

(51) Int. Cl.
*A61B 17/04* (2006.01)
(52) U.S. Cl. .................. 606/232; 623/13.11
(58) Field of Classification Search ........... 606/232; 623/13.11, 13.12–13.14
See application file for complete search history.

(56) References Cited

U.S. PATENT DOCUMENTS

| | | | |
|---|---|---|---|
| 1,806,162 A | 5/1931 | Hahn |
| 4,235,238 A | 11/1980 | Ogiu et al. |
| 5,139,520 A | 8/1992 | Rosenberg |
| 5,210,911 A | 5/1993 | Brown |
| 5,306,301 A | 4/1994 | Graf et al. |
| 5,374,269 A | 12/1994 | Rosenberg |
| 5,569,306 A | 10/1996 | Thal |
| 5,645,588 A | 7/1997 | Graf et al. |
| 5,683,419 A | 11/1997 | Thal |
| 5,709,708 A | 1/1998 | Thal |
| 5,720,765 A | 2/1998 | Thal |
| 5,728,136 A | 3/1998 | Thal |
| 6,024,758 A | 2/2000 | Thal |
| 6,143,017 A | 11/2000 | Thal |
| 6,156,039 A | 12/2000 | Thal |
| RE037,963 E | 1/2003 | Thal |
| 6,520,980 B1 | 2/2003 | Foerster |
| 6,524,317 B1 | 2/2003 | Ritchart et al. |
| 6,533,802 B2 | 3/2003 | Bojarski et al. |
| 6,582,453 B1 | 6/2003 | Tran et al. |
| 6,585,730 B1 | 7/2003 | Foerster |

(Continued)

OTHER PUBLICATIONS

2002, Smith & Nephew; Meniscal Repair with FastFix Suture System. *Surgical Techniques* 1-8 Pages.

(Continued)

*Primary Examiner*—(Jackie) Tan-Uyen T. Ho
*Assistant Examiner*—Gregory A Anderson
(74) *Attorney, Agent, or Firm*—David W. Meibos; Barbar Daniels; Daniel F. Justin

(57) ABSTRACT

A system for attaching soft tissue to bone includes an anchor, a suture, and a tissue retainer. The anchor may have a threaded tip that engages the bone, and a suture retention portion with passageways arranged such that each of first and second anchor portions of the suture can be drawn through the passageways along only a single direction. The tissue retainer has passageways through which the suture can freely move in either direction. Thus, the anchor and the tissue retainer may be attached to bone and tissue, respectively, and the suture may be drawn to substantially irreversibly draw the bone and tissue together. In alternative embodiments, an anchor may receive only one portion of suture and/or one suture end may be affixed to the anchor. The anchor may alternatively permit free motion of the suture, while the tissue retainer permits passage of the suture along only one direction.

60 Claims, 15 Drawing Sheets

U.S. PATENT DOCUMENTS

| | | |
|---|---|---|
| 6,652,561 B1 | 11/2003 | Tran |
| 6,656,183 B2 | 12/2003 | Colleran et al. |
| 6,660,008 B1 | 12/2003 | Foerster et al. |
| 6,692,516 B2 | 2/2004 | West, Jr. et al. |
| 6,770,076 B2 | 8/2004 | Foerster |
| 2002/0019649 A1 | 2/2002 | Sikora et al. |
| 2002/0111653 A1 | 8/2002 | Foerster |
| 2002/0128684 A1 | 9/2002 | Foerster |
| 2003/0130694 A1 | 7/2003 | Bojarski et al. |
| 2003/0144696 A1* | 7/2003 | Sinnott et al. ............ 606/232 |
| 2003/0195563 A1 | 10/2003 | Foerster |
| 2004/0015171 A1 | 1/2004 | Bojarski et al. |
| 2004/0098053 A1 | 5/2004 | Tran |
| 2004/0111117 A1 | 6/2004 | Colleran et al. |
| 2007/0233241 A1 | 10/2007 | Graf et al. |

OTHER PUBLICATIONS

2002, Smith & Nephew; Fast Fix Meniscal Repair System. *Catalog* pp. H-52-H-53.

2004, Smith & Nephew; ACL/PCL Fixation Systems. *Catalog* pp. H-36.

2004, Smith & Nephew; Rotator Cuff Repair. *Catalog* pp. 1-4.

Jun. 2003, Linvatec; UltraFix Knotless. *Surgical Technique* 1-16 pages.

2002, Linvatec; Arthroscopic Soft Tissue Fixation. *Surgical Technique* 1-6 pages.

2001, Mitek; RapidLoc, Meniscal Repair System. Product Information.

Oct. 2004, Mitek; RapidLoc. *Surgical Technique* 1-3 pages.

Feb. 1998, Innovasive Devices; Y-Knot. *Product Information* 2 pages.

Aug. 2003, Opus Medical; The AutoCuff System. *Product Information* 4 pages.

2002, Arthrex; TissueButton. *Product Information* 1 page.

1999, Arthrotek; RCB-Rotator Cuff Buttress. *Product Information* 2 pages.

\* cited by examiner

SYSTEM AND METHOD FOR ANCHORING SUTURE TO BONE

CROSS-REFERENCE TO RELATED APPLICATIONS

None.

BACKGROUND OF THE INVENTION

1. The Field of the Invention

The present invention relates generally to devices for anchoring soft tissue to bone, and more precisely, to devices that secure suture to the bone and soft tissue.

2. The Relevant Technology

There are a number of surgical procedures in which it is necessary to draw soft tissue and bone together. One such procedure is rotator cuff repair, in which the connective tissue of the displaced rotator cuff is to be drawn against the bone of the shoulder until the joint is able to heal properly.

A variety of anchoring systems are presently used to carry out such procedures. Unfortunately, many known systems are somewhat unwieldy, unreliable, or difficult to implant in the patient. Some such systems require the surgeon to take some type of action to lock the suture at its desired length. Thus, the surgeon must keep the suture at the desired length while carrying out the locking operation. If the suture length changes during locking, the surgeon may need to perform additional steps to adjust the length of the suture. Furthermore, many such systems have excessive components that must be implanted into the body.

Accordingly, a need exists for systems and methods for attaching soft tissue to bone that remedy the shortcomings of the prior art. More particularly, there is a need for a system that is compact, has relatively few components, and is easily lockable during surgery.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems that can be used to draw a bone and a portion of soft tissue together. By increasing the size of the line locks, it is also appreciated that the line locks can be used outside of surgical procedures for any use where it is desired to selectively tighten a line such as a rope, cord, string, or other conventional type of line that extends between two objects, or to bring the two objects closer together.

In this application, the term "attach" is broadly interpreted to include securement of separate elements to each other, and the integral formation of separate elements with each other. Thus, two portions of an object that are unitarily formed in a single operation may be said to be "attached" together. The term "symmetry," without modification, includes any known type of symmetry, including mirror symmetry across a plane and radial symmetry about an axis.

The term "direction," when used in connection with motion of a flexible member such as a line, does not necessarily refer to a static vector. Rather, a "direction" may refer to motion of the line along a pathway, toward one specified end of the pathway. Thus, stating that a line is only able to move along a pathway in one direction means that the line can only be advanced toward one end of the pathway. The line moves along the pathway in one direction even though in the course of advancement along the pathway, segments of the line will simultaneously be moving along a variety of differently-oriented vectors.

A "long axis" refers to an axis of symmetry or extension along which an object has a length that is substantially its largest dimension. The term "retain" refers to limiting relative motion between two objects in some manner. The term "locking" refers to fixation of the relative positions of two objects in such a manner that relative translation or rotation along or about at least one axis is substantially prevented along at least one direction until the objects have been unlocked.

Figure 1:
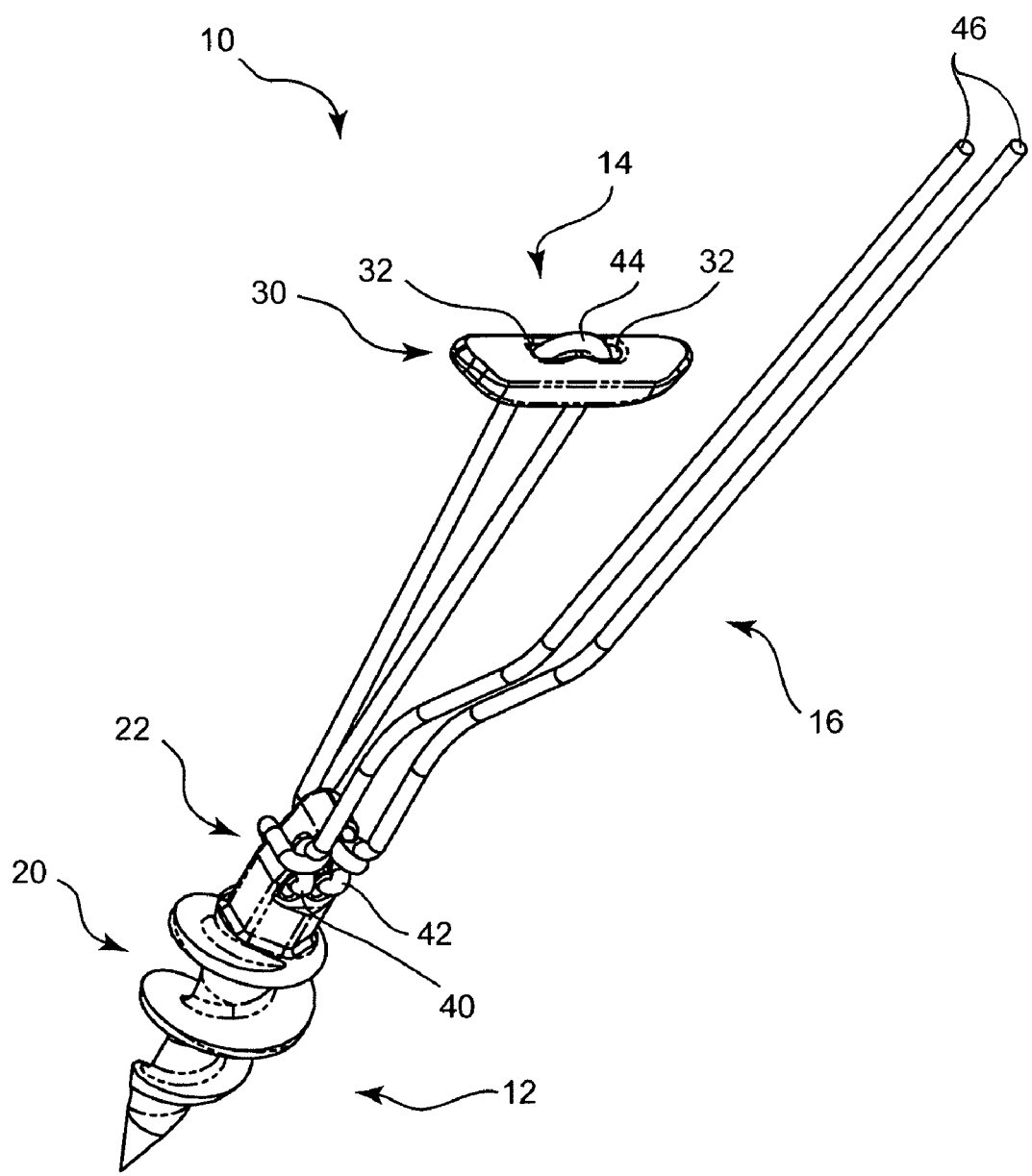
FIG. 1 is a perspective view of an attachment system according to one embodiment of the invention, with an anchor, a tissue retainer, and a suture threaded through the anchor and the tissue retainer.

Referring to FIG. 1, a perspective view illustrates a system 10 according to one embodiment of the invention. The system 10 may be used to attach soft tissue (not shown in FIG. 1) to bone (also not shown in FIG. 1). According to one example, the system 10 may be used to attach a torn rotator cuff to the bone of the shoulder to promote proper healing of the shoulder joint.

In the embodiment of FIG. 1, the system 10 includes an anchor 12, a tissue retainer 14, and a suture 16 that couples the tissue retainer 14 to the anchor 12. The anchor 12 is designed to be implanted in bone, and the tissue retainer 14 is designed to be inserted through an opening in the tissue and then drawn toward the anchor 12 by the suture 16 to draw the soft tissue toward the bone.

As shown, the anchor 12 includes a bone retention portion 20 and a suture retention portion 22. The bone retention portion 20 is designed to be embedded into the bone in such a manner that the bone retention portion 20 securely fastens the anchor 12 to the bone. The suture retention portion 22 is designed to retain a portion of the suture 16 in such a manner that, when the suture 16 is under tension, the suture 16 can only be drawn through the suture retention portion 22 in a manner that brings the tissue retainer 14 closer to the anchor 12. The configuration and operation of the bone retention portion 20 and the suture retention portion 22 will be shown and described in greater detail subsequently.

The tissue retainer 14 has a body 30 with a relatively elongated shape designed to be insertable through a relatively small opening in the soft tissue. The elongated shape is further designed to abut the tissue on the opposite side of the small opening in such a manner that, in response to tension on the suture 16, the tissue retainer 14 is able to draw the soft tissue toward the anchor 12. The body 30 bounds two passageways 32, which may be sized and arranged to permit relatively free passage of the suture 16 therethrough along either direction. The present invention is not limited to the tissue retainer configuration illustrated in FIG. 1; rather, a wide variety of shapes and sizes may be used.

The suture 16 has a first anchor portion 40 and a second anchor portion 42, both of which pass through the suture retention portion 22 of the anchor 12. The suture 16 further has a retainer portion 44 that passes through the passageways 32 of the tissue retainer 14. Additionally, the suture 16 has two working ends 46 that are available to be drawn by the surgeon to induce motion of the first and second anchor portions 40, 42 through the suture retention portion 22, thereby drawing the tissue retainer 14 toward the anchor 12.

Figure 2:
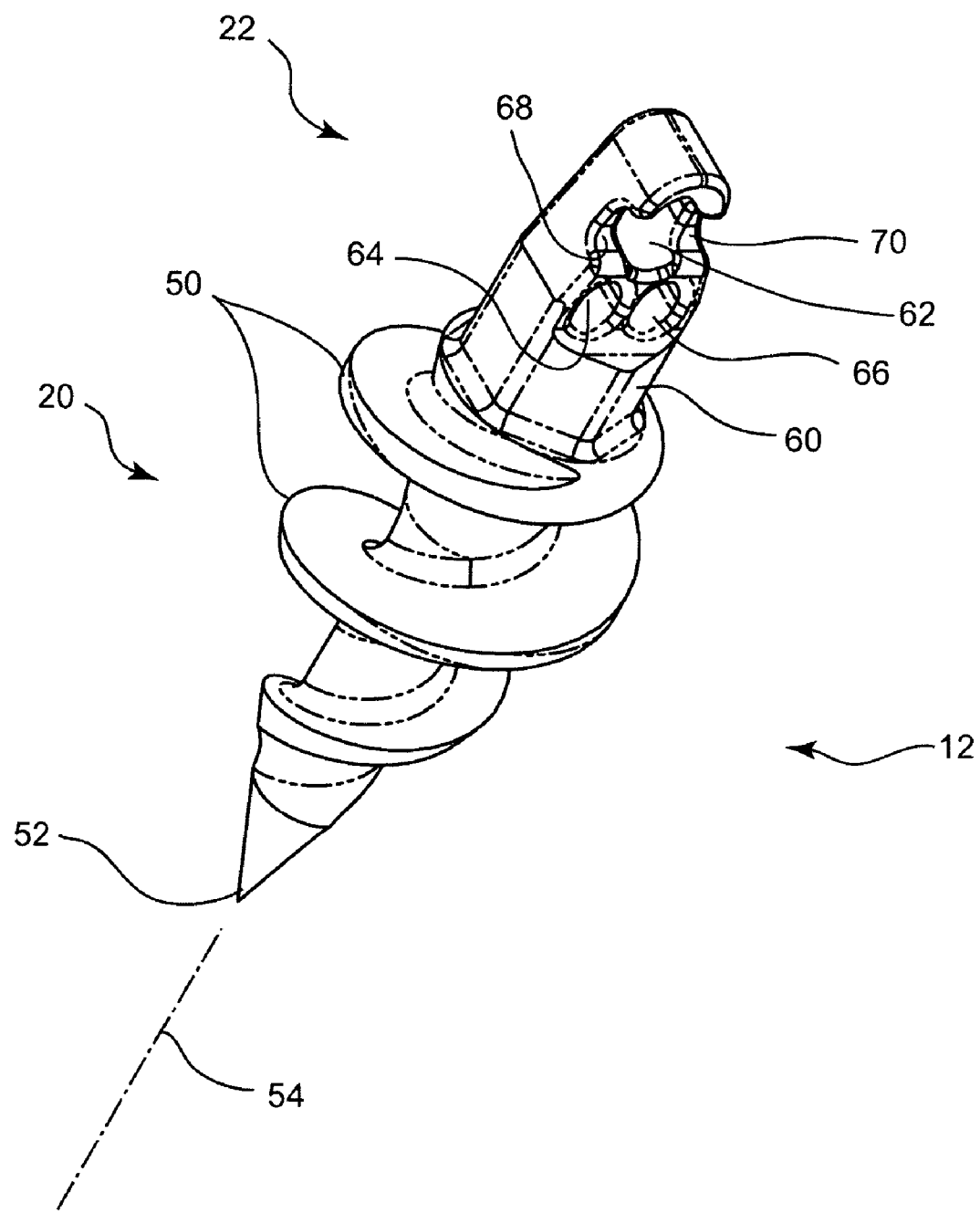
FIG. 2 is a perspective view of the anchor of FIG. 1, in isolation.

Referring to FIG. 2, a perspective view illustrates the anchor 12 of the system 10 of FIG. 1 in isolation. As illustrated, the bone retention portion 20 has a plurality of threads 50 that extend outward to engage the bone. The bone retention portion 20 also has a sharpened end 52. The anchor 12 has a long axis 54 about which the threads 50 extend along a generally helical, tapered path. The threads 50 may be "self-tapping," or shaped to form their own canal in the bone in response to torque and pressure of the sharpened end 52 against the surface of the bone. Alternatively, the threads 50 may be shaped to rotate into engagement with a pre-formed and/or pre-tapped aperture formed in the bone.

As yet another alternative, an anchor according to the invention may be retained in bone via other mechanisms. For example, an anchor according to the invention may be configured as a "tack" with a sharpened end that penetrates the bone sufficiently for retention. Such an anchor may optionally be driven into the bone at an angle, or driven into the bone and subsequently rotated, to enhance retention. Alternatively, such an anchor may be barbed or may have fold-out wings or other structures designed to block withdrawal of the anchor from the bone. Any bone retention structure known in the art may be used in combination with the other inventive features disclosed herein.

The anchor 12 is substantially rigid, and therefore does not depend upon flexion of any part of the anchor 12 to enable retention of the anchor 12 in the bone. The anchor 12 may be formed of a biocompatible metal such as titanium. Alternatively, a bioabsorbable material or a nonbioabsorbable polymer may be used to form the anchor 12.

In the embodiment of FIG. 2, the suture retention portion 22 has a hexagonal collar 60 designed to be insertable into a hexagonal bore of a driver (not shown) such that the driver is able to impart torque as well as axial pressure to the anchor 12. The suture retention portion 22 bounds a primary passageway 62, a first secondary passageway 64, and a second secondary passageway 66. A first notch 68 and a second notch 70 extend outward from opposite sides of the primary passageway 62. The first and second notches 68, 70 extend at right angles to the primary passageway 62, and are therefore oriented generally perpendicular to the primary passageway 62. The notches 68, 70 cooperate with the passageways 62, 64, 66 to lock the suture 16 against motion through the suture retention portion 22 along one direction, as will be further explained in connection with FIGS. 3 and 4.

Figure 3:
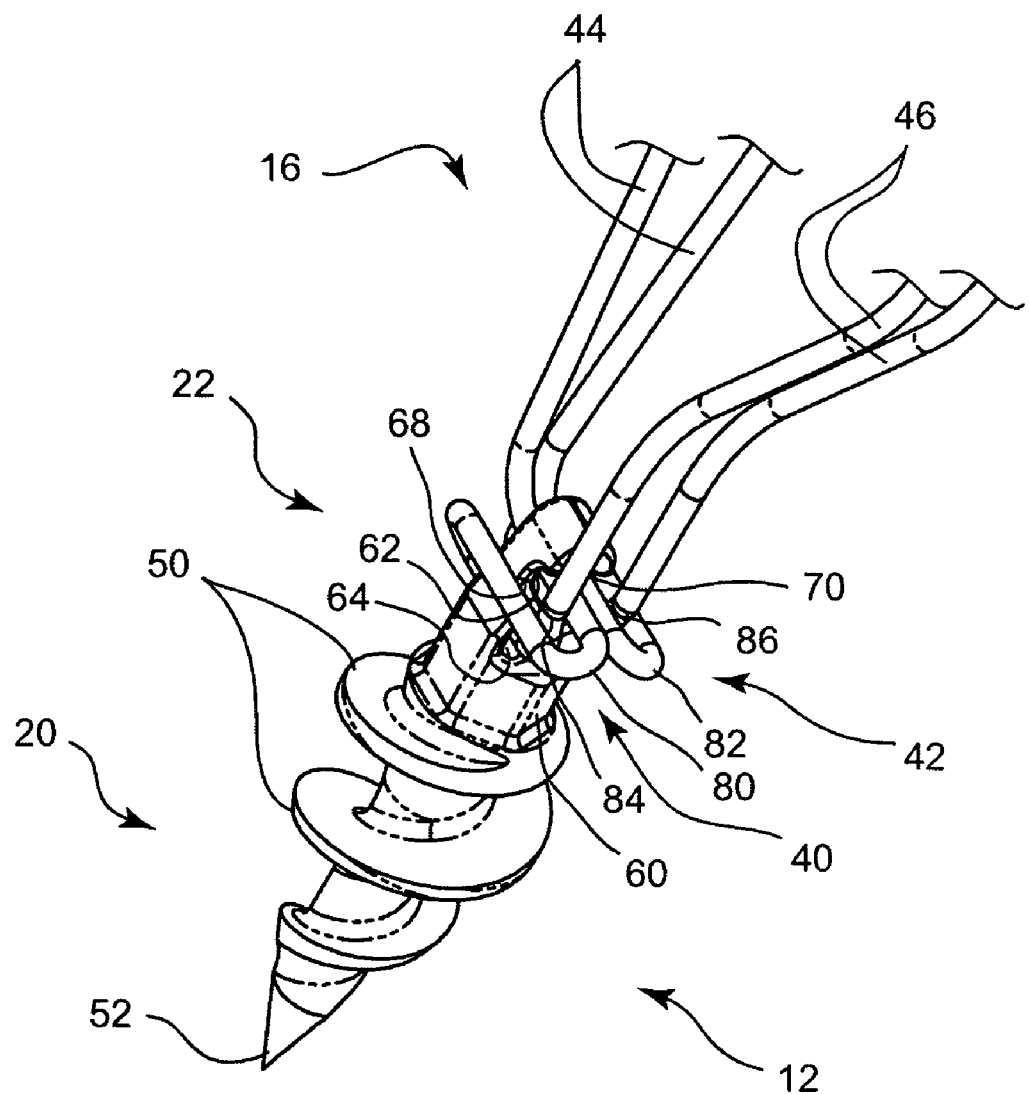
FIG. 3 is a perspective view of the anchor of FIG. 1, with the suture threaded loosely through the passageways of the suture retention portion of the anchor.

Referring to FIG. 3, a perspective view illustrates the anchor 12 with a portion of the suture 16. As shown, the first and second anchor portions 40, 42 of the suture 16 are inserted relatively loosely through the passageways 62, 64, 66 of the suture retention portion 22. From the tissue retainer 14 (not shown in FIG. 3), the first and second anchor portions 40, 42 pass through the primary passageway 62, and then extend outward generally parallel to the first and second notches 68, 70, respectively. The first and second anchor portions 40, 42 define first and second compression sections 80, 82 as they pass over the first and second notches 68, 70, respectively.

The first and second anchor portions 40, 42 then pass around the sides of the suture retention portion 22, and then through the first and second secondary passageways 64, 66, respectively. From the first and second secondary passageways 64, 66, the first and second anchor portions 40, 42 are routed toward the primary passageway 62. The first and second anchor portions 40, 42 then extend between the first and second compression sections 80, 82 and the first and second notches 68, 70, respectively. First and second compressed sections 84, 86 are thereby defined in the first and second anchor portions 40, 42, at the locations where the first and second anchor portions 40, 42 extend underneath the first and second compression sections 80, 82, respectively.

Figure 4:
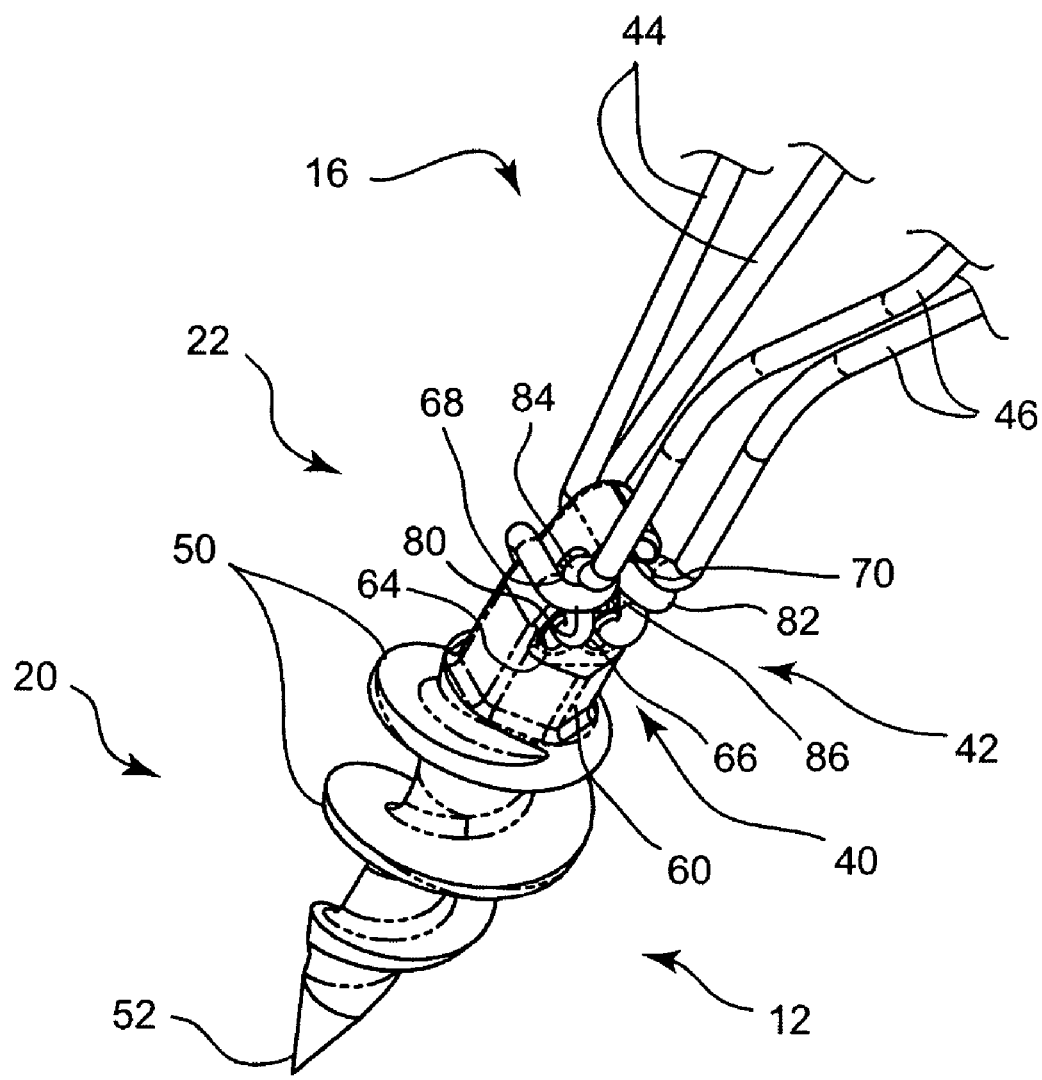
FIG. 4 is a perspective view of the anchor of FIG. 1, with the suture threaded tightly through the passageways of the suture retention portion of the anchor.

Referring to FIG. 4, a perspective view illustrates the anchor 12 with a portion of the suture 16 threaded relatively tightly through the passageways 62, 64, 66 of the suture retention portion 22. Substantially all of the slack has been removed from the first and second anchor portions 40, 42. Consequently, the first and second compressed sections 84, 86 extend through the first and second notches 68, 70, respectively, and are held against the notches 68, 70 by the first and second compression sections 80, 82, respectively.

As the compressed sections 84, 86 conform to the shapes of the notches 68, 70, respectively, the notches 68, 70 serve to create additional bends in the corresponding compressed sections 84, 86 to enhance retention of the anchor portions 40, 42 by the anchor 12. Such bends enhance locking of the compressed sections 84, 86 because there is greater friction keeping the compressed sections 84, 86 in place. Furthermore, there is no direct path along which tension on the working portions 46 can act to draw the compressed sections 84, 86 through the space between the compression sections 80, 82 and the notches 68, 70, respectively.

The result of the manner in which the suture 16 is routed through the passageways 62, 64, 66 is that the first and second anchor portions 40, 42 can be drawn through the passageways 62, 64, 66 in a manner that brings the tissue retainer 14 closer to the anchor 12, but not in a manner that permits the tissue retainer 14 and the anchor 12 to move apart. Tension tending to pull the tissue retainer 14 away from the anchor 12 increases the magnitude of the force by which the compressed sections 84, 86 are pressed into the notches 68, 70 by the compression sections 80, 82, respectively.

Conversely, tension on the working portions 46 of the suture 16 tends to pull the compressed sections 84, 86 free of the notches 68, 70, respectively, to permit motion of the anchor portions 40, 42 through the passageways 62, 64, 66 to draw the tissue retainer 14 closer to the anchor 12. When the tension on the working portions 46 abates, the compressed sections 80, 82 are again pressed into the notches 68, 70 due to tension in the portion of the suture 16 between the anchor 12 and the tissue retainer 14.

The first and second anchor portions 40, 42 can also be independently drawn through the passageways 62, 64, 66. More precisely, a surgeon can draw only the working portion 46 adjacent to the first anchor portion 40 to pull the first compressed section 84 free of the first notch 68, thereby permitting the first anchor portion 40 to advance through the primary passageway 62 and the first secondary passageway 64 along a direction that draws the tissue retainer 14 closer to the anchor 12. Similarly, a surgeon can draw only the working portion 46 adjacent to the second anchor portion 42 to pull the second compressed section 86 free of the second notch 70, thereby permitting the second anchor portion 42 to advance through the primary passageway 62 and the second secondary passageway 66 along a direction that draws the tissue retainer 14 closer to the anchor 12.

The two portions of the suture 16 that extend between the tissue retainer 14 (shown in FIG. 1) and the anchor 12 remain substantially the same length because suture is able to pass relatively freely from one portion to the other through the passageways 32 of the tissue retainer 14. Drawing only one of the working portions 46 provides a mechanical advantage that moves the tissue retainer 14 only half as fast as drawing both working portions 46, thereby facilitating fine-tuning of the position of the soft tissue and the level of tension in the suture 16. Furthermore, the ability to draw only one of the working portions 46 provides the surgeon with additional operating flexibility.

Figure 5:
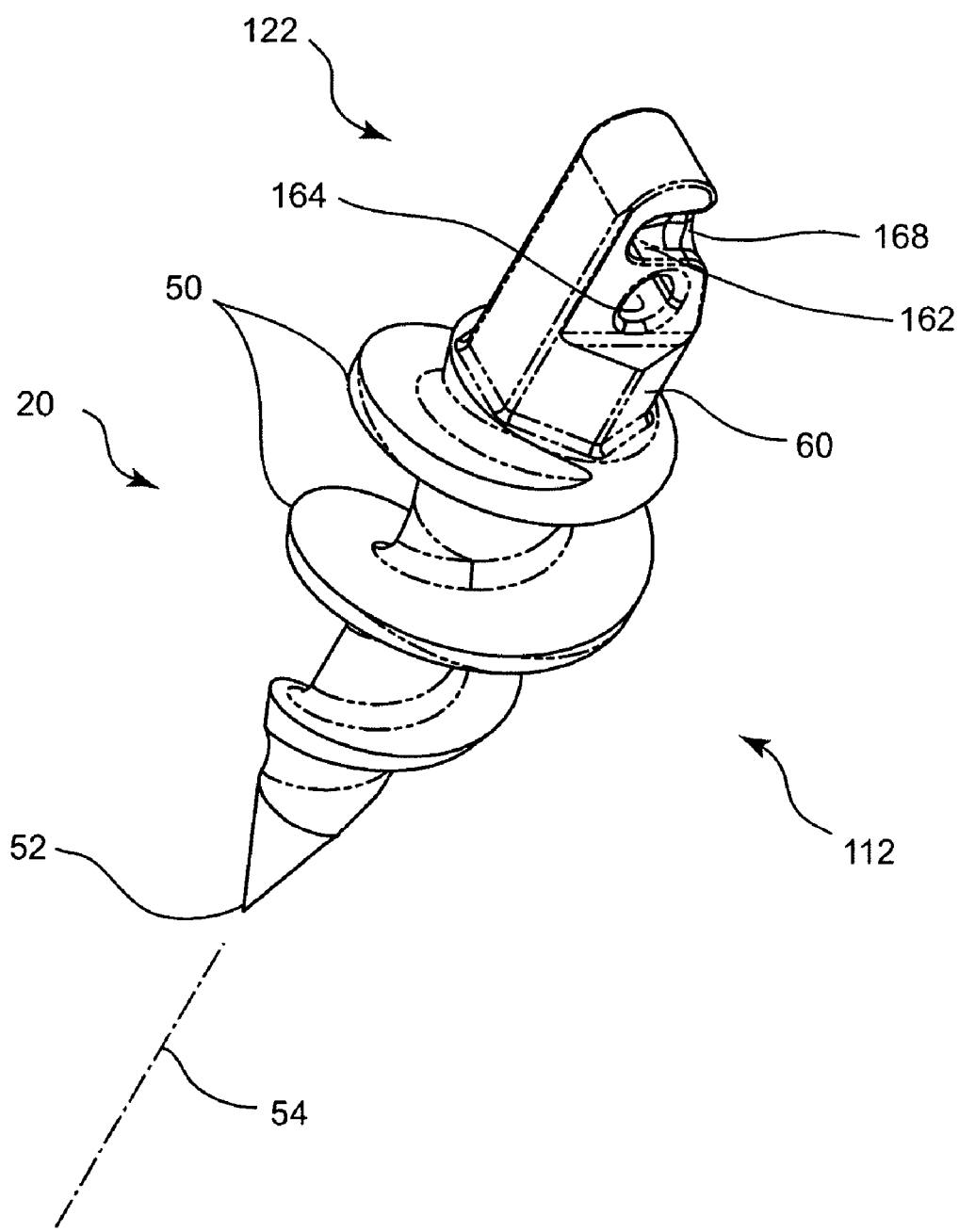
FIG. 5 is a perspective view of an anchor of an attachment system of one alternative embodiment of the invention.

Referring to FIG. 5, a perspective view illustrates an anchor 112 according to one alternative embodiment of the invention. As shown, the anchor 112 has a bone retention portion 20 and a suture retention portion 122. The bone retention portion 20 may be substantially identical to that of the anchor 12 of FIGS. 1 through 4. However, the tissue retention portion 122 is configured differently from the tissue retention portion 22 of the previous embodiment.

More precisely, the suture retention portion 122 has a hexagonal collar 60 like that of the previous embodiment. However, in place of the passageways 62, 64, 66, the suture retention portion 122 has a primary passageway 162 and a secondary passageway 164. The suture retention portion 122 also has a notch 168 that extends generally perpendicular to the primary passageway 162 in a manner similar to that of the second notch 70 of the previous embodiment. The anchor 112 is thus designed to receive and lock only one suture portion in a manner that will be shown and described in connection with FIG. 6.

Figure 6:
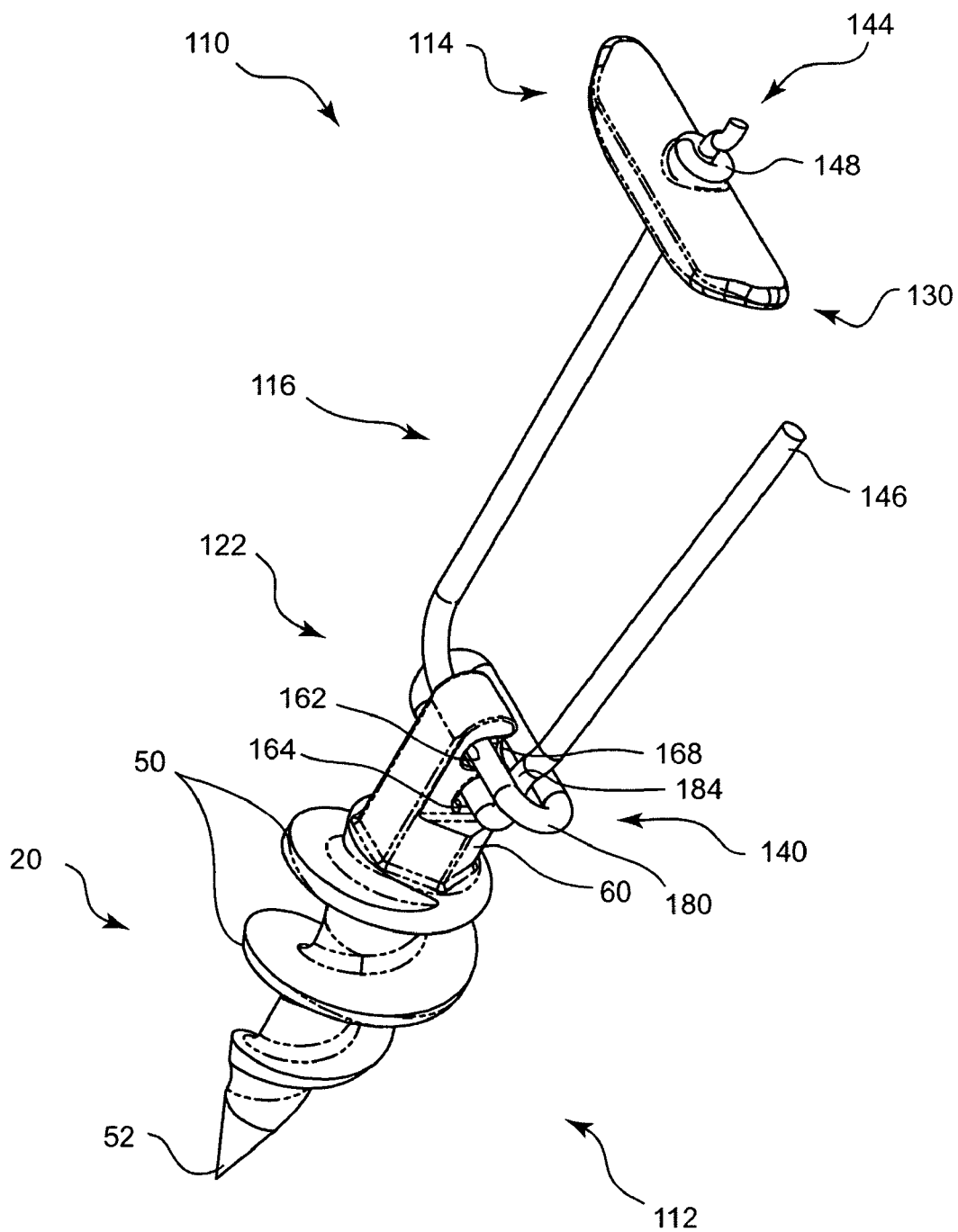
FIG. 6 is a perspective view of the anchor of FIG. 5 with the suture threaded loosely through the passageways of the suture retention portion of the anchor.

Referring to FIG. 6, a perspective view illustrates a system 110 that includes the anchor 112 as well as a tissue retainer 114 and a suture 116. Like the tissue retainer 14, the tissue retainer 114 has a body 130 that bounds a passageway (not shown) through which the suture 116 passes. The suture 116 may be similar to that of the suture 16 of the previous embodiment.

In the embodiment of FIG. 6, the suture 116 has an anchor portion 140 that is received by the suture retention portion 122 of the anchor 112. Additionally, the suture 116 has a retainer portion 144 that is secured to the tissue retainer 114 and a working end 46 that can be manipulated by the surgeon to draw the tissue retainer 114 toward the anchor 112. The retainer portion 144 may be secured to the tissue retainer 114 via a knot 148. According to alternative embodiments, bonding, insert molding, application of rigid fasteners, or the like may be used in place of the knot 148 to secure the retainer portion 144 to the tissue retainer 114.

From the tissue retainer 114, the anchor portion 140 of the suture 116 passes through the primary passageway 162, and then extends along the notch 168 to define a compression section 180 of the anchor portion 140. The anchor portion 140 then extends around the suture retention portion 122 and through the secondary passageway 164. From the secondary passageway 164, the anchor portion 140 extends between the compression section 180 and the notch 168 to define a compressed section 184 that will be pressed into the notch 168 by the compression section 180 when the suture 116 is tensioned.

Figure 7:
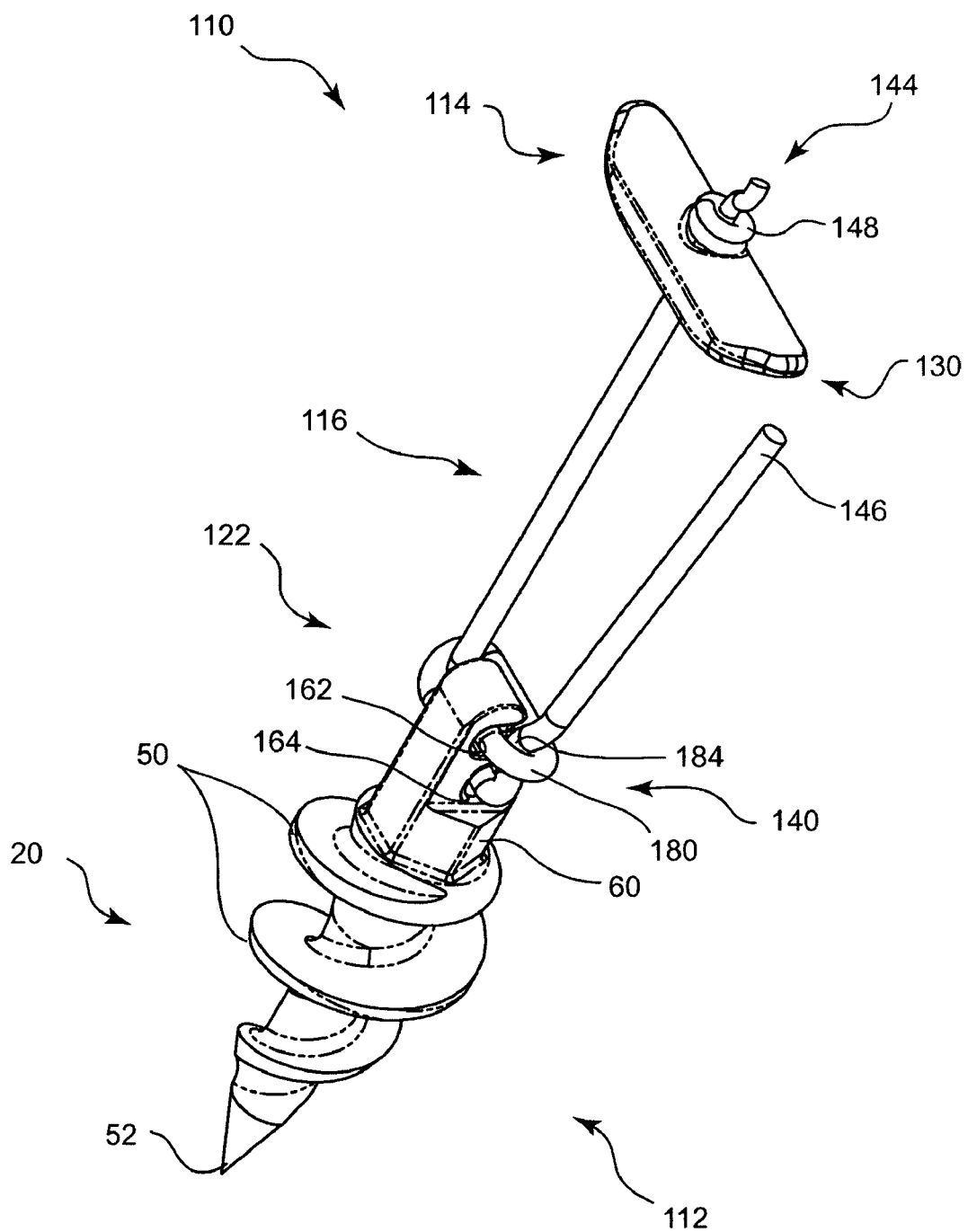
FIG. 7 is a perspective view of the anchor of FIG. 5 with the suture threaded tightly through the passageways of the suture retention portion of the anchor.

Referring to FIG. 7, a perspective view illustrates the system 110 of FIG. 6, with the suture 116 routed relatively tightly through the suture retention portion 122 of the anchor 112. As in the previous embodiment, the compressed section 184 conforms to the shape of the notch 168, and the notch 168 thereby serves to create additional bends in the compressed section 184 to enhance retention of the anchor portion 140 by the anchor 112.

Like the suture retention portion 22 of the previous embodiment, the suture retention portion 122 of the anchor 112 retains the anchor portion 140 in a manner that permits motion of the anchor portion 140 through the passageways 162, 164 along only one direction. More precisely, tension tending to pull the tissue retainer 114 away from the anchor 112 increases the magnitude of the force by which the compressed section 184 is pressed into the notch 168 by the compression section 180. Conversely, tension on the working portion 146 of the suture 116 tends to pull the compressed section 184 free of the notch 168 to permit motion of the anchor portion 140 through the passageways 162, 164 to draw the tissue retainer 114 closer to the anchor 112. When the tension on the working portion 146 abates, the compressed section 180 is again pressed into the notch 168 due to tension in the portion of the suture 116 between the anchor 112 and the tissue retainer 114.

Thus, the surgeon is able to draw the tissue retainer 114 closer to the anchor 112 by simply pulling on the working portion 146. The one-way locking provided by the suture retention portion 122 keeps the tissue retainer 114 from moving apart from the anchor 112. The system 110 may be particularly useful in applications in which a more compact anchor is desired, and in which the strength of double-suturing is not needed.

Figure 8:
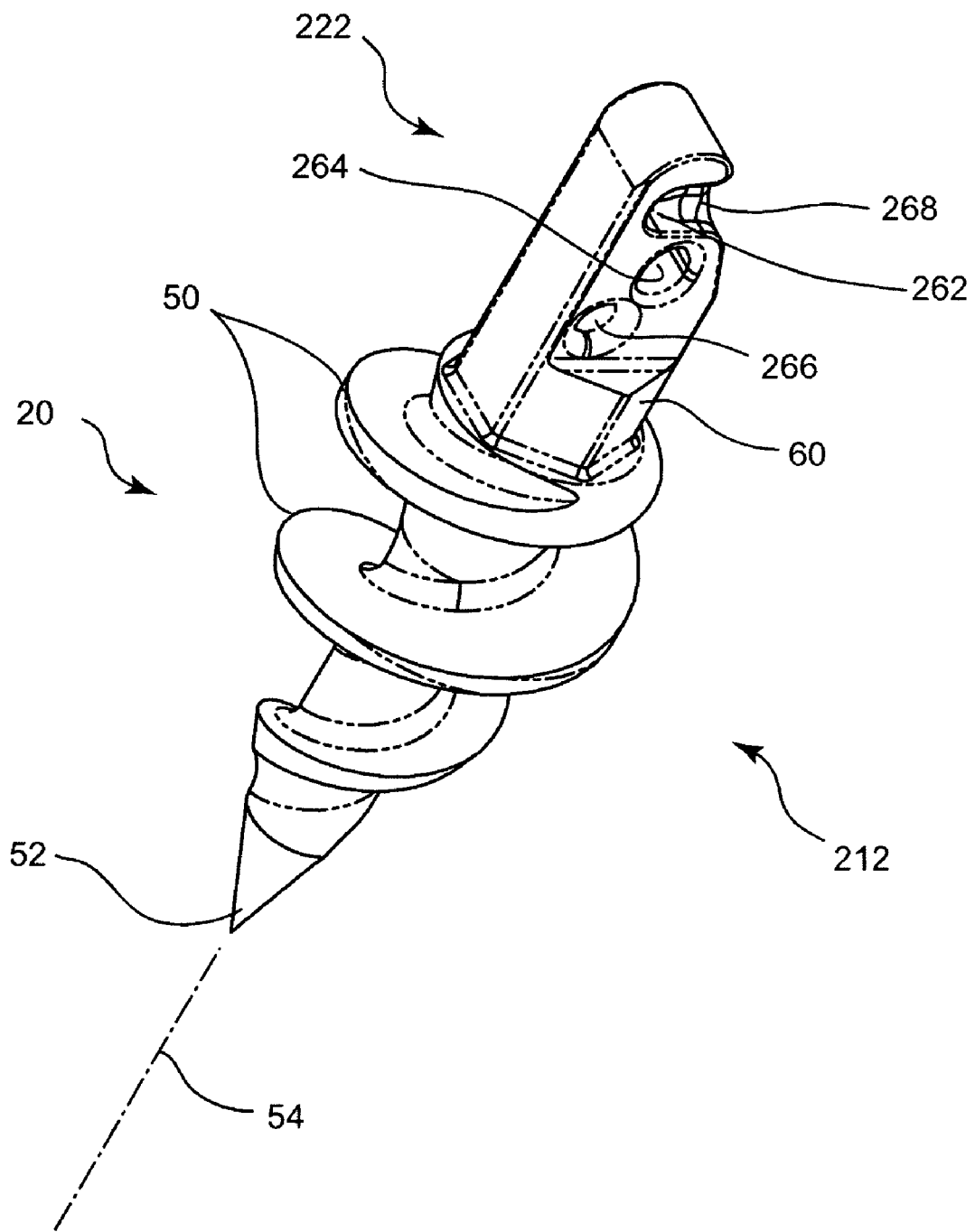
FIG. 8 is a perspective view of an anchor of an attachment system of another alternative embodiment of the invention.

Referring to FIG. 8, a perspective view illustrates an anchor 212 according to another alternative embodiment of the invention. As shown, the anchor 212 has a bone retention portion 20, which may be substantially identical to those of the previous two embodiments. Additionally, the anchor 212 has a suture retention portion 222. The suture retention portion 222 has a hexagonal collar 60 like those of the previous embodiments, but is otherwise configured differently from the suture retention portions 22, 122 of the previous embodiments.

Additionally, the anchor 212 has a primary passageway 262, a secondary passageway 264, and a retention passageway 266. The suture retention portion 222 also has a notch 268 that extends generally perpendicular to the primary passageway 262 in a manner similar to that of the second notch 70 of the first embodiment. The anchor 212 is thus designed to receive two suture portions, and to lock via the retention passageway 266, and to lock the other in a manner similar to that of the previous embodiments, as will be shown and described in connection with FIG. 9.

Figure 9:
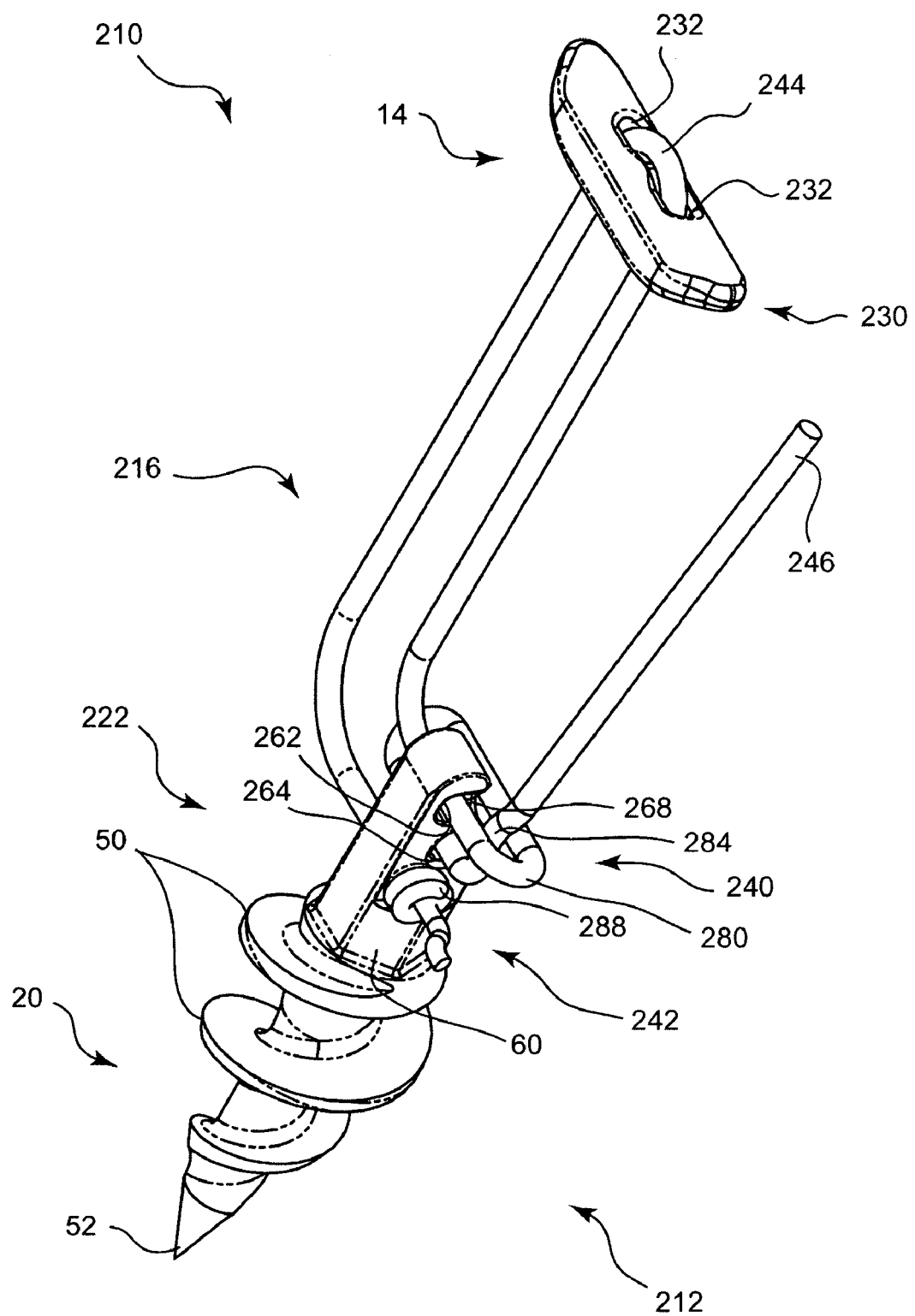
FIG. 9 is a perspective view of the anchor of FIG. 8 with the suture threaded loosely through the passageways of the suture retention portion of the anchor.

Referring to FIG. 9, a perspective view illustrates a system 210 that includes the anchor 212 as well as a tissue retainer 14 and a suture 216. The tissue retainer 14 may be substantially identical to that of the first embodiment, and thus has a body 30 that bounds two passageways 32 through which the suture 216 passes. The suture 216 may be similar to that of the suture 16 of the first embodiment.

In the embodiment of FIG. 9, the suture 216 has a first anchor portion 240 and a second anchor portion 242, each of which is received by the suture retention portion 222 of the anchor 212. Additionally, the suture 216 has a retainer portion 244 that is secured to the tissue retainer 14 and a working end 246 that can be manipulated by the surgeon to draw the tissue retainer 14 toward the anchor 212. The retainer portion 244 may pass through the passageways 32 of the tissue retainer 14 in a manner that permits relatively free motion of the retainer portion 244 therethrough.

From the tissue retainer 14, the first anchor portion 240 of the suture 216 passes through the primary passageway 262, and then extends along the notch 268 to define a compression section 280 of the first anchor portion 240. The first anchor portion 240 then extends around the suture retention portion 222 and through the secondary passageway 264. From the secondary passageway 264, the first anchor portion 240 extends between the compression section 280 and the notch 268 to define a compressed section 284 that will be pressed into the notch 268 by the compression section 280 when the suture 216 is tensioned.

The second anchor portion 242 of the suture 216 passes through the retention passageway 266 (not visible in FIG. 9). A knot 288 is formed in the second anchor portion 242 to keep the second anchor portion 242 from being withdrawn from the retention passageway 266 toward the tissue retainer 14. Thus, the second anchor portion 242 is secured to the suture retention portion 222 in a manner that maintains tension in the suture 216 between the anchor 212 and the tissue retainer 14. In alternative embodiments, bonding, insert molding, application of rigid fasteners, or the like may be used in place of the knot 288 to secure the second anchor portion 242 to the retention passageway 266.

Figure 10:
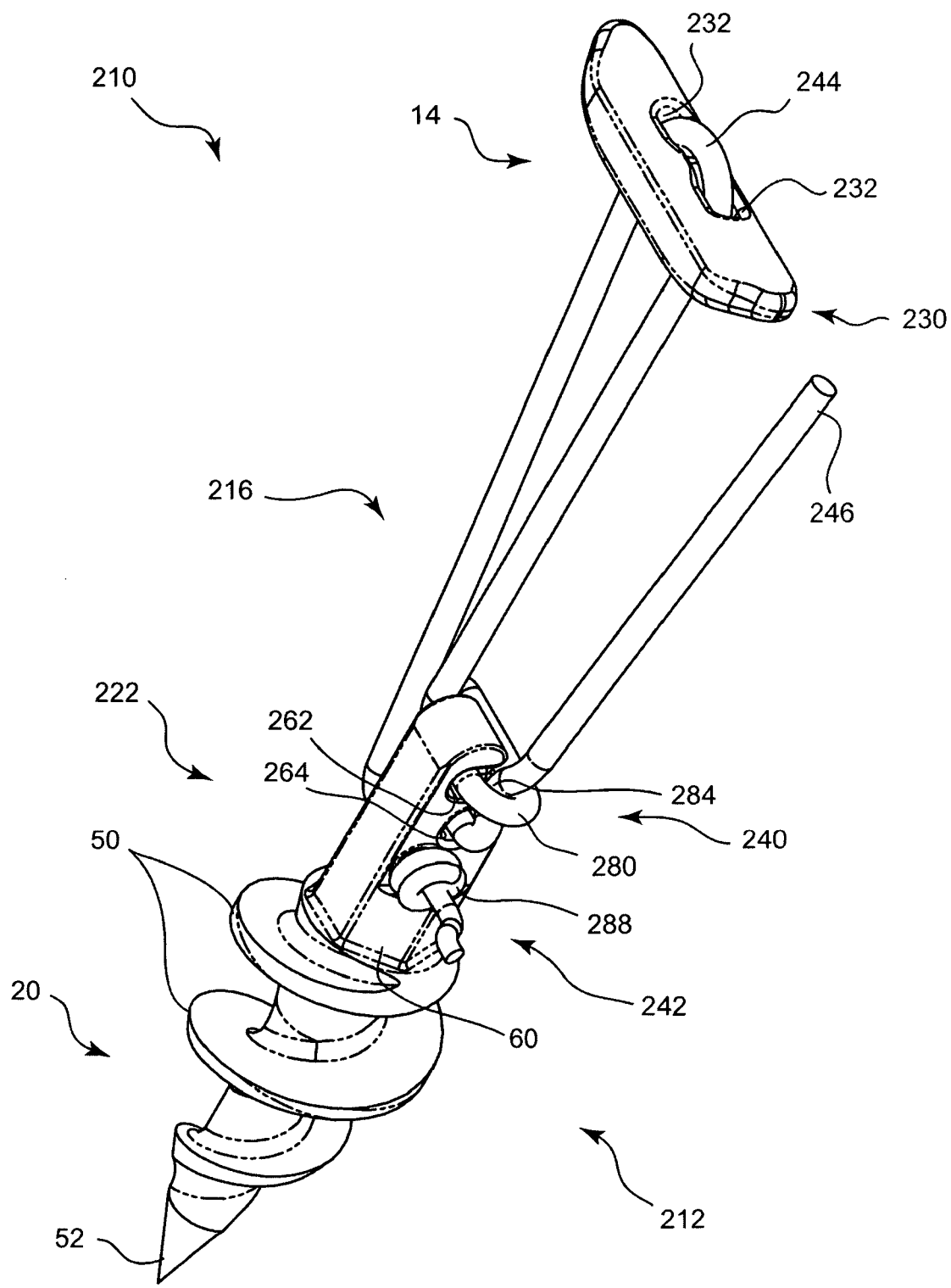
FIG. 10 is a perspective view of the anchor of FIG. 8 with the suture threaded tightly through the passageways of the suture retention portion of the anchor.

Referring to FIG. 10, a perspective view illustrates the system 210 of FIG. 9, with the suture 216 routed relatively tightly through the suture retention portion 222 of the anchor 212. As in the previous embodiment, the compressed section 284 conforms to the shape of the notch 268, and the notch 268 thereby serves to create additional bends in the compressed section 284 to enhance retention of the first anchor portion 240 by the anchor 212.

Like the suture retention portion 22 of the first embodiment, the suture retention portion 222 of the anchor 212 retains the first anchor portion 240 in a manner that permits motion of the anchor portion 240 through the passageways 262, 264 along only one direction. More precisely, tension tending to pull the tissue retainer 14 away from the anchor 212 increases the magnitude of the force by which the compressed section 284 is pressed into the notch 268 by the compression section 280. The first anchor portion 240 is therefore unable to move through the suture retention portion 222. The second anchor portion 242 is locked in place due to abutment of the knot 248 against the portion of the suture retention portion 222 that surrounds the retention passageway 266.

Conversely, tension on the working portion 246 of the suture 216 tends to pull the compressed section 284 free of the notch 268 to permit motion of the first anchor portion 240 through the passageways 262, 264 to draw the tissue retainer 14 closer to the anchor 212. When the tension on the working portion 246 abates, the compressed section 280 is again pressed into the notch 268 due to tension in the portion of the suture 216 between the anchor 212 and the tissue retainer 14.

Thus, the surgeon is able to draw the tissue retainer 14 closer to the anchor 212 by simply pulling on the working portion 246. The one-way locking provided by the suture retention portion 222 keeps the tissue retainer 14 from moving apart from the anchor 212. Free motion of the retainer portion 244 through the passageways 32 of the tissue retainer 14 enables the portions of the suture 216 between the anchor 212 and the tissue retainer 14 to remain at substantially the same length as the tissue retainer 14 is drawn toward the anchor 212.

Figure 11:
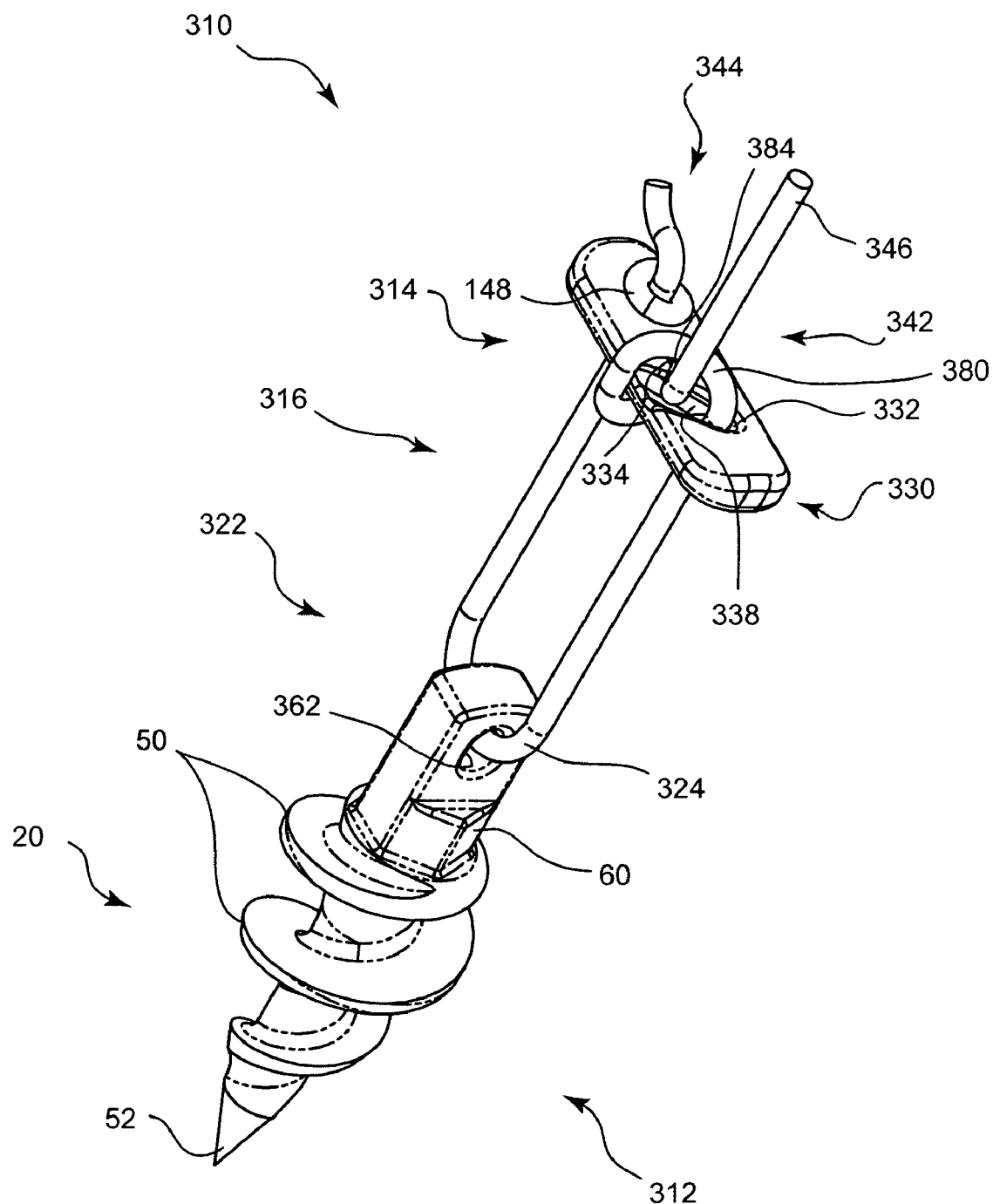
FIG. 11 is a perspective view of an attachment system according to another embodiment of the invention.

In the systems 10, 110, 210 of the preceding figures, the anchor provides the mechanism by which a suture can be drawn only in one direction, i.e., to bring the anchor and tissue retainer closer together, but not to permit them to move apart. However, in alternative embodiments of the invention, such functionality may instead be provided by the tissue retainer. FIG. 11 provides one exemplary embodiment in which one-way suture motion is provided by the tissue retainer instead of the anchor.

Referring to FIG. 11, a perspective view illustrates a system 310 according to another alternative embodiment of the invention. As shown, the system 310 includes an anchor 312, a tissue retainer 314, and a suture 316. The anchor 312 has a bone retention portion 20, which may be identical to that of the first embodiment, and a suture retention portion 322 that is configured differently from those of the previous embodiments. More precisely, the suture retention portion 322 is designed to permit relatively free passage of the suture 316 along either direction, while the tissue retainer 314 permits motion of the suture 316 along substantially only one direction.

More specifically, the suture retention portion 322 has a passageway 324 through which the suture 316 extends. The passageway 324 does not restrict motion of the suture 316 along either direction. The tissue retainer 314 has a body 330 that bounds a first passageway 332, a second passageway 334, and a retention passageway (not visible). The body 330 further comprises a notch 338 that extends generally perpendicular to the first passageway 332.

The suture 316 has an anchor portion 340 that passes through the passageway 324 of the suture retention portion of the anchor 312. Additionally, the suture 316 has a first retainer portion 342 and a second retainer portion 344, both of which are retained by the tissue retainer 314. The first and second retainer portions 342, 344 are retained in a manner that permits motion of the first retainer portion 342 only in a direction that draws the tissue retainer 314 closer to the anchor 312. The suture 316 has a working portion 346 that can be manipulated to draw the tissue retainer 314 toward the anchor 312.

The first retainer portion 342 passes through the first and second passageways 332, 334 in a manner similar to that of the first and second anchor portions 240, 242 of the embodiment of FIG. 9 to enable motion of the first retainer portion 342 through the passageways 332, 334 along only one direction. Thus, a compression section 380 and a compressed section 384 are defined in the first retainer portion 342. As in previous embodiments, the compression section 380 extends generally parallel to the notch 338, and the compressed section 384 passes between the compression section 380 and the notch 338. In response to tension in the anchor portion 340, the compression section 380 presses the compressed section 384 against the notch 338. Consequently, bends are formed in the compressed section 384 to enhance locking of the first retainer portion 342.

A knot 148 is provided in the second retainer portion 344 to keep the second retainer portion 344 from being withdrawn through the retention passageway (not shown) in response to tension on the anchor portion 340. In alternative embodiments, bonding, insert molding, application of rigid fasteners, or the like may be used in place of the knot 148 to secure the second retainer portion 344 to the retention passageway.

In order to tighten the tissue retainer 314 against the anchor 312, the surgeon simply pulls on the working portion 346. The one-way locking provided by the tissue retainer 314 keeps the tissue retainer 314 from moving apart from the anchor 312. Free motion of the anchor portion 340 through the passageway 324 of the anchor portion 322 enables the portions of the suture 316 between the anchor 312 and the tissue retainer 314 to remain at substantially the same length as the tissue retainer 314 is drawn toward the anchor 312. Accordingly, although the tissue retainer 314 provides one-way suture locking instead of the anchor 312, the embodiment of FIG. 11 provides easy tightening of tissue against bone in a manner similar to that of the previous embodiments.

Figure 12:
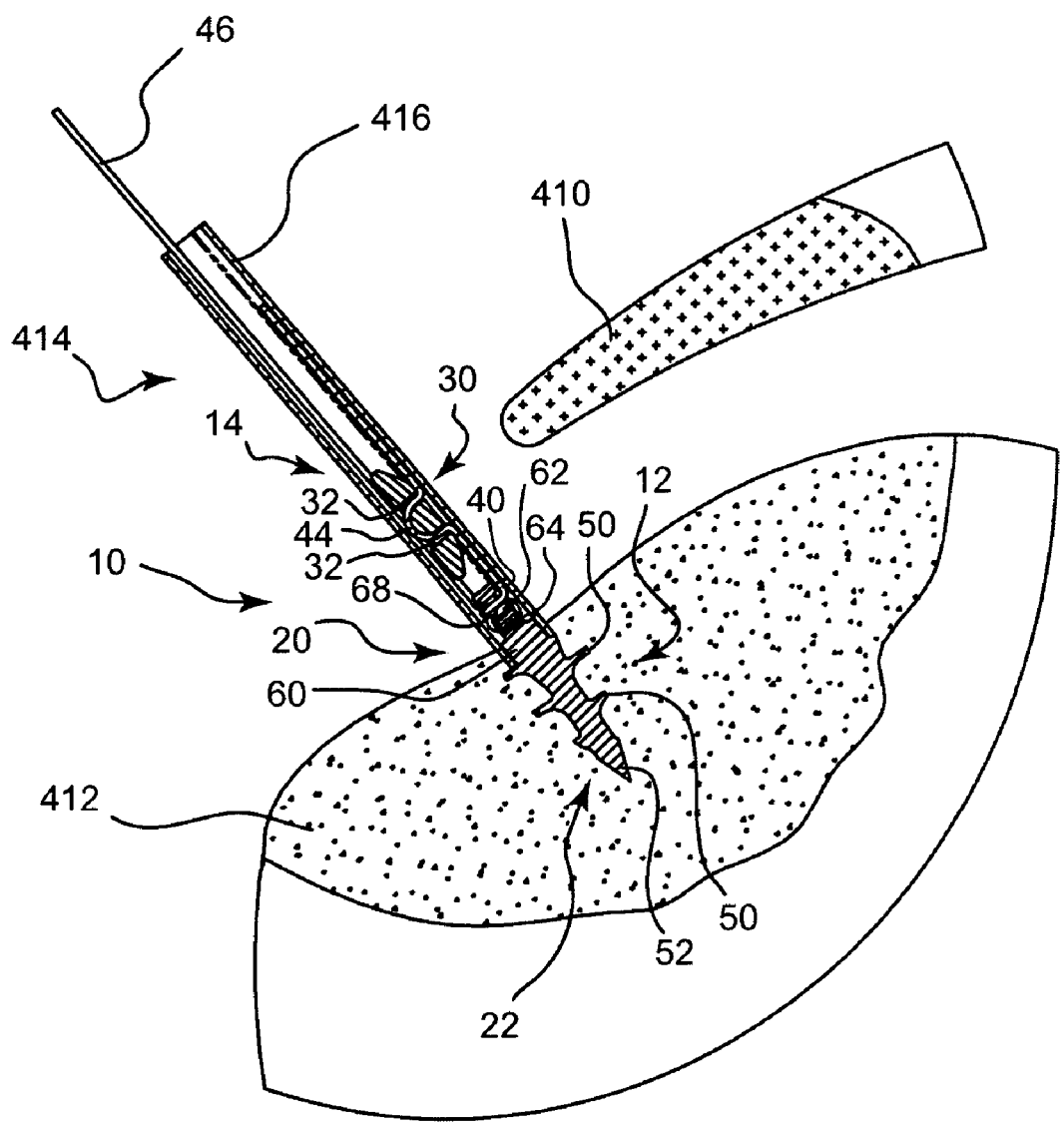
FIG. 12 is a front elevation, section view of the attachment system of claim 1, with the anchor in the process of being implanted into the bone of a shoulder.

Referring to FIG. 12, a front elevation, partially sectioned view illustrates an initial step in the usage of the system 10 of FIGS. 1 through 4 to attach a piece of soft tissue 410 to a bone 412. The soft tissue 410 may be a piece of connective tissue, skin, or the like. According to one exemplary method of use, the soft tissue 410 may be a rotator cuff, and the bone 412 may be part of the corresponding shoulder bone, such as the right shoulder of a patient, as viewed from the front. For clarity, a portion of the bone 412 and the soft tissue 410 have been partially sectioned, and the various elements of the system 10 have been sectioned substantially in their entirety.

FIG. 12 illustrates insertion of the anchor 12 into the bone 412 through the use of an inserter 414, which may have a hollow shape that defines a bore 416 with a generally hexagonal cross section. The tissue retainer 14 is positioned within the bore 416, and the suture 16 extends out of the bore 416 at one end to leave the working portions 46 exposed. The hexagonal collar 60 of the anchor 12 is retained in the opposite end of the bore 416 such that the hexagonal cross section of the bore 416 causes the anchor 12 to rotate in response to rotation of the inserter 414. The inserter 414 may have a handle or the like (not shown) to facilitate manual rotation thereof. If desired, the system 10 may be factory assembled within the inserter 414, as illustrated in FIG. 12, so that a surgeon need not insert the hexagonal collar 60 into the bore 416 prior to surgical use.

In order to implant the anchor 12 in the bone 412, the sharpened end 52 of the inserter may be pressed against the surface of the bone 412 and rotated clockwise via the inserter 414. The sharpened end 52 may then penetrate the bone 412, and the threads 50 may engage the bone such that the anchor 12 cannot be withdrawn from the bone 412 in the absence of relative rotation in the opposite direction. In alternative embodiments, the anchor 12 need not be self-tapping. Rather, a drill, reamer, or the like may be used to form a channel in the bone 412, and the channel may optionally be tapped prior to insertion of the anchor 412 to facilitate insertion of the anchor 412.

After the anchor 12 has reached the proper position, the inserter 414 is withdrawn to leave the anchor 12 embedded securely in the bone 412. Then, the tissue retainer 14 may be inserted through the soft tissue 410, as will be shown and described in connection with FIG. 13.

Figure 13:
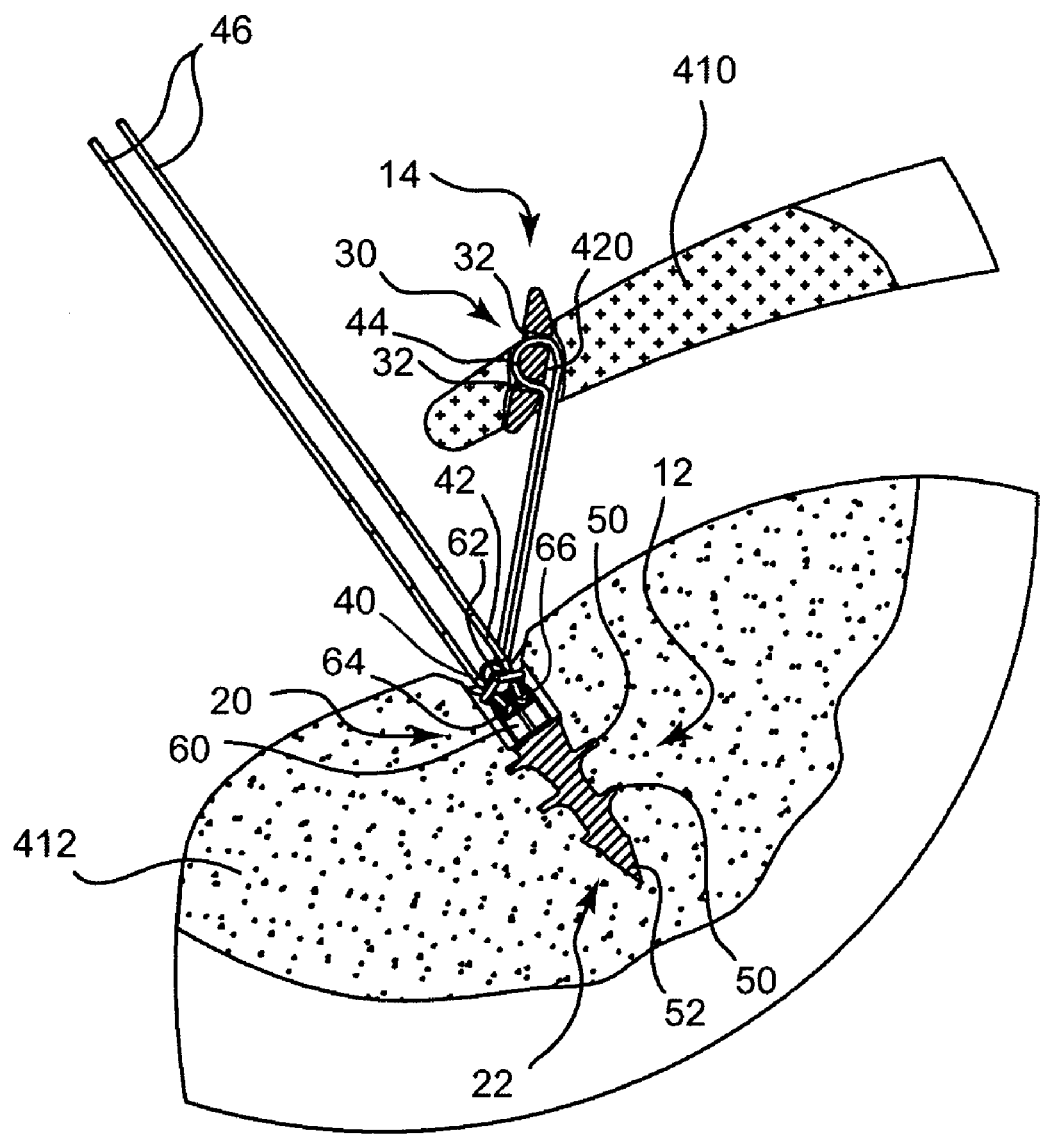
FIG. 13 is a front elevation, section view of the attachment system of claim 1, with the anchor implanted in the bone of the shoulder and the tissue retainer in the process of being inserted through an opening in the rotator cuff.

Referring to FIG. 13, a front elevation, partial section view illustrates another step of an exemplary method of using the system 10 to attach the soft tissue 410 and the bone 412 together. For clarity, the suture 16 and a portion of the anchor 12 have not been sectioned in FIG. 13. This format will also be followed in FIGS. 14 and 15. As shown, an opening 420 has been formed in the soft tissue 410. The opening may be formed via a needle, cannula, or the like.

According to one alternative embodiment, a tissue retainer (not shown) may have a generally sharpened shape selected to permit the tissue retainer to be pressed into the soft tissue 410 to penetrate the soft tissue 410, thereby forming the opening 420. The tissue retainer may be pushed into place by hand, or via an inserter designed to retain a trailing end of the tissue retainer so that a sharpened leading edge can be pressed through the soft tissue 420.

Returning to the embodiment shown in FIG. 13, a cannulated inserter (not shown) different from the inserter 414 may optionally be used to puncture the soft tissue 410 to form the opening 420. Such a cannulated inserter may also contain the tissue retainer 14 to facilitate insertion of the tissue retainer 14 through the soft tissue 410. The end of the cannulated inserter may simply be inserted through the opening 420, and a plunger within the cannulated inserter may be actuated to eject the tissue retainer 14 so that the tissue retainer 14 remains on the proper side of the soft tissue 410 after withdrawal of the end of the cannulated inserter from the opening 420.

According to alternative steps, the tissue retainer 14 may be inserted through the opening 420 by manually positioning it within the opening 420, and then pressing it through with a rod or other rigid insertion device. Once the tissue retainer 14 has passed through the opening 420, it may tend to reorient itself into an orientation parallel to the soft tissue 410 in response to tension on the suture 16, as will be illustrated in connection with FIG. 14.

Figure 14:
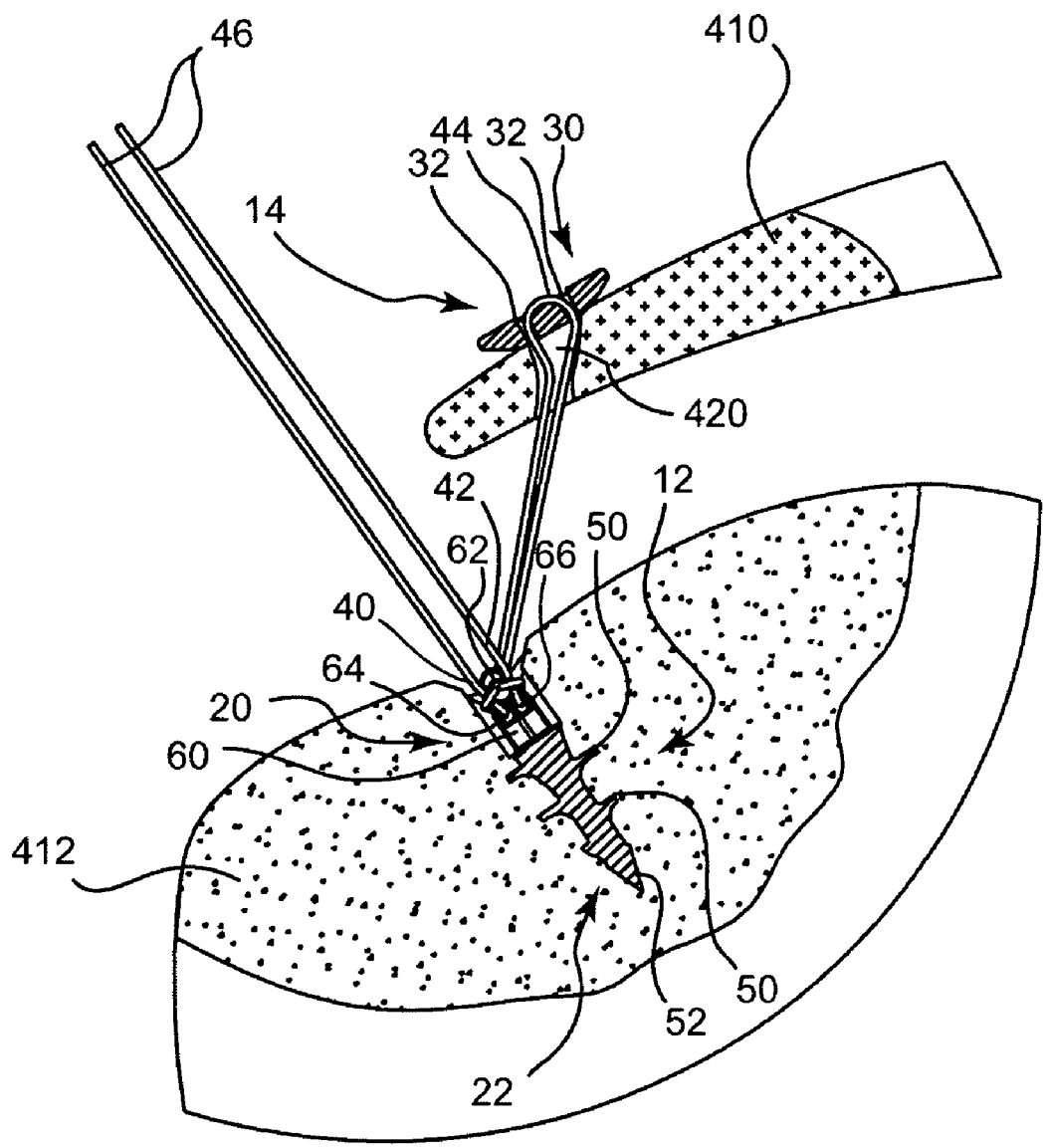
FIG. 14 is a front elevation, section view of the attachment system of claim 1, with the anchor and the tissue retainer in place.

Referring to FIG. 14, a front elevation, partial section view illustrates another step of an exemplary method of using the system 10 to attach the soft tissue 410 and the bone 412 together. As shown, the tissue retainer 14 has passed fully through the opening, and is oriented generally parallel to the soft tissue 410. The working ends 46 may be pulled slightly to provide tension in the portion of the suture 16 between the anchor 12 and the tissue retainer 14 to draw the tissue retainer 14 into the orientation of FIG. 14.

Due to its elongated shape, when oriented as in FIG. 14, the tissue retainer 14 is too long to pass back through the opening 420. Accordingly, as long as tension remains in the portion of the suture 16 between the tissue retainer 14 and the anchor 12, the tissue retainer 14 will remain generally in the orientation illustrated. Further tension may be applied to draw the soft tissue 410 toward the bone 412, as will be shown in FIG. 15.

Figure 15:
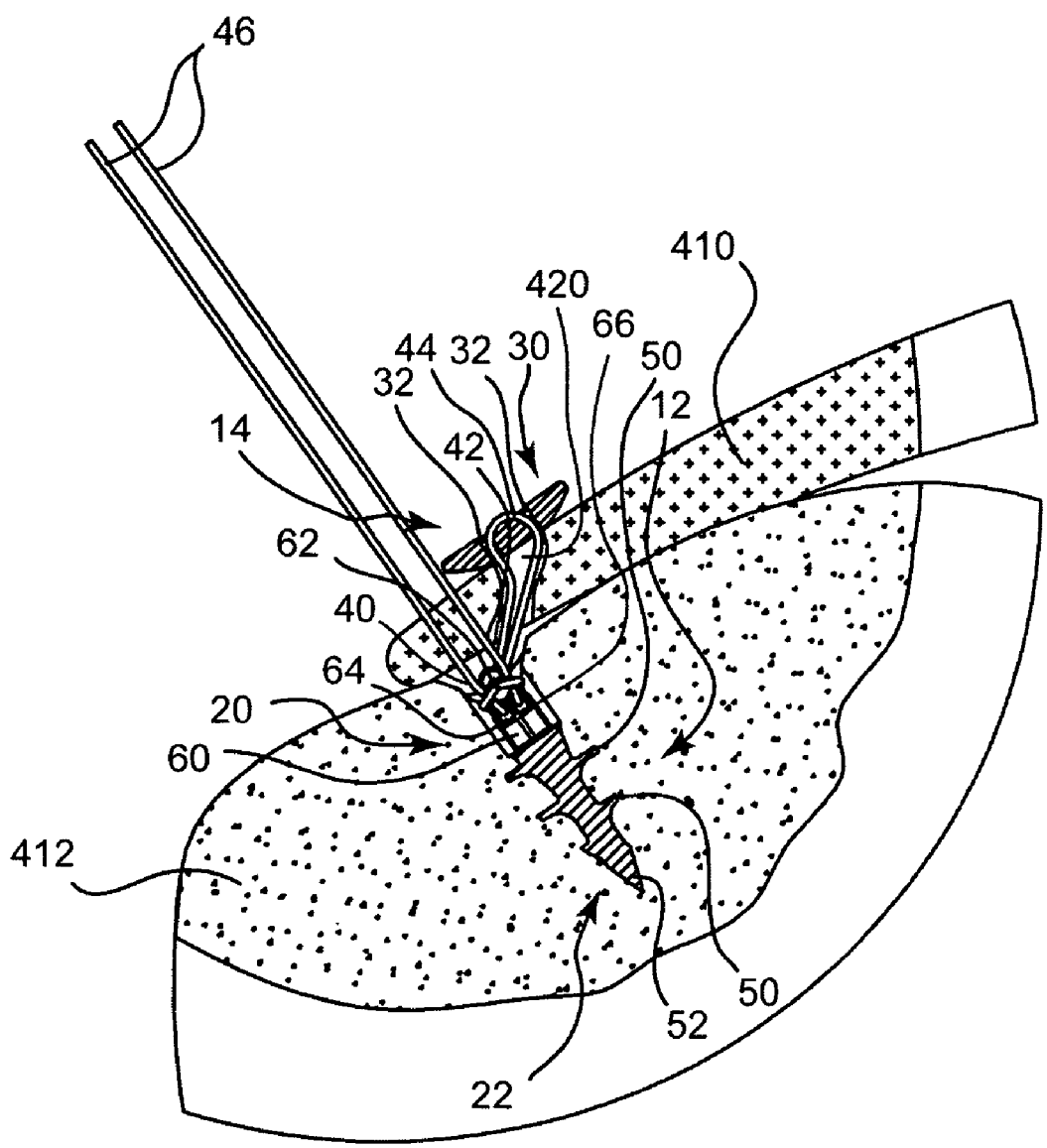
FIG. 15 is a front elevation, section view of the attachment system of claim 1, with the anchor and the tissue retainer in place, and with the suture drawn taught to attach the rotator cuff to the bone.

Referring to FIG. 15, a front elevation, partial section view illustrates the soft tissue 410 and the bone 412, drawn and secured together via the system 10. As shown, further tension has been applied to the working ends 46 to cause the first and second anchor portions 40, 42 to move through the passageways 62, 64, 66 of the anchor 12, thereby shortening the portion of the suture 16 between the tissue retainer 14 and the anchor 12.

As described previously, the passageways 62, 64, 66 and the notches 68, 70 (not visible in FIG. 15) are configured such that the anchor portions 40, 42 are only able to move through the passageways 62, 64, 66 along one direction, i.e., the direction corresponding to motion of the tissue retainer 14 toward the anchor 12. Relief of tension on the working portions 46 does not result in motion of the soft tissue 410 back away from the anchor 412. Accordingly, the working portions 46 may be drawn by degrees until the soft tissue 410 is sufficiently close to the bone 412, as desired by the surgeon. Once the soft tissue 410 has been drawn to the appropriate position, the working ends 46 may be cut short, and the first and second anchor portions 40, 42 will remain engaged by the anchor 12 to keep the soft tissue 410 in place.

The present invention has particular relevance to surgery, and more particularly to tissue retention through the use of sutures. However, the principles, structures, and methods of the present invention may also be extended to other fields, including the use of larger anchors for locking ropes or cables in a wide variety of applications.

The present invention may be embodied in other specific forms without departing from its spirit or essential characteristics. For example, above are described various alternative examples of different tissue anchoring systems. It is appreciated that various features of the anchoring systems can be mixed and matched to form a variety of other alternatives, each of which may have a different suture threading system, tissue retainer, and/or bone retention structure according to the invention. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for attaching a bone and a tissue together via a suture, the system comprising:
   a suture;
   an anchor comprising:
      a bone retention portion shaped to engage the bone to attach the anchor to the bone; and
      a first suture retention portion attached to the bone retention portion, wherein the first suture retention portion is configured to retain a first anchor portion of the suture; and
   a tissue retainer comprising a second suture retention portion configured to retain a retainer portion of the suture;
   wherein at least one of the first suture retention portion and the second suture retention portion comprises a plurality of passageways arranged to define a first pathway;
   wherein the suture is routed through the passageways such that the first anchor portion of the suture is able to be drawn along the first pathway substantially along only a first direction;
   wherein the first anchor portion is further routed along the first pathway such that a first compression section of the first anchor portion presses another part of the first anchor portion against the first suture retention portion of the anchor in response to tension urging the first anchor portion to move along the first pathway opposite to the first direction.

2. The system of claim 1, wherein the bone retention portion comprises a substantially rigid structure shaped to engage the bone to rigidly attach the anchor to the bone.

3. The system of claim 2, wherein the bone retention portion comprises a threaded tip comprising a plurality of threads shaped to engage the bone to attach the anchor to the bone.

4. The system of claim 1, wherein the suture further comprises a second anchor portion, wherein the suture is further routed through the passageways such that the second anchor portion of the suture is able to be drawn through at least some of the passageways substantially along only a second direction, wherein the second anchor portion is spaced apart from the first anchor portion, wherein the second anchor portion comprises a second compression section that presses another part of the second anchor portion against the first suture retention portion in response to tension urging the second anchor portion to move through the passageways opposite to the second direction, wherein the first suture retention portion is configured to retain the first and second anchor portions.

5. The system of claim 4, wherein the first suture retention portion comprises the plurality of passageways, wherein the passageways further define a second pathway along which the second anchor portion of the suture can be advanced only along a direction that draws the anchor and the tissue retainer closer together.

6. The system of claim 5, wherein the second suture retention portion comprises one or more passageways through which the retainer portion is relatively freely movable along either direction.

7. The system of claim 5, wherein the first and second anchor portions are able to be independently drawn along the first and second pathways, respectively.

8. The system of claim 5, wherein the passageways comprise a primary passageway, a first secondary passageway, and a second secondary passageway, wherein the first pathway passes through the primary passageway and the first secondary passageway, and the second pathway passes through the primary passageway and the second secondary passageway.

9. The system of claim 1, wherein the first suture retention portion comprises the plurality of passageways, wherein the plurality of passageways comprises two passageways symmetrically displaced from each other across a long axis of the anchor.

10. The system of claim 1, wherein at least one of the first suture retention portion and the second suture retention portion comprises a notch positioned adjacent to the passageways to receive a first compressed section of the suture such that the first compressed section is compressed against the notch by the first compression section of the suture to substantially prevent motion of the suture through the passageways in a manner that permits the tissue retainer to move apart from the anchor.

11. The system of claim 1, wherein the anchor is formed of a metal.

12. The system of claim 1, wherein the anchor is formed of a bioabsorbable material.

13. The system of claim 1, wherein the anchor is formed of a non-bioabsorbable polymer.

14. A system for attaching a bone and a tissue together via a suture, the system comprising:
   a suture; and
   an anchor comprising:
      a bone retention portion comprising a substantially rigid structure shaped to engage the bone to rigidly attach the anchor to the bone; and
      a suture retention portion attached to the bone retention portion, the suture retention portion comprising a plurality of passageways arranged to define a first pathway;

wherein the suture is routed through the passageways such that a first anchor portion of the suture is able to be drawn along the first pathway substantially along only a first direction;

wherein the first anchor portion is further routed along the first pathway such that a first compression section of the first anchor portion presses another part of the first anchor portion against the first suture retention portion in response to tension urging the first anchor portion to move along the first pathway opposite to the first direction.

15. The system of claim 14, wherein the bone retention portion comprises a threaded tip having a plurality of threads shaped to engage the bone to attach the anchor to the bone.

16. The system of claim 15, wherein the threaded tip comprises a sharpened shape selected to permit the bone anchor to penetrate the bone in response to pressure of the threaded tip against the bone.

17. The system of claim 14, wherein the suture further comprises a second anchor portions, wherein the second anchor portion extends along a second pathway along which the second anchor portion under tension can only be advanced in a second direction, wherein the second anchor portion comprises a second compression section that presses another part of the second anchor portion against the first suture retention portion in response to tension urging the second anchor portion to move along the second pathway opposite to the second direction.

18. The system of claim 17, wherein the first and second anchor portions are able to be independently drawn along the first and second pathways, respectively.

19. The system of claim 17, wherein the passageways comprise a primary passageway, a first secondary passageway, and a second secondary passageway, wherein the first pathway passes through the primary passageway and the first secondary passageway, and the second pathway passes through the primary passageway and the second secondary passageway.

20. The system of claim 14, wherein the plurality of passageways comprises two passageways symmetrically displaced from each other across a long axis of the anchor.

21. The system of claim 14, wherein the suture retention portion comprises a notch positioned adjacent to the passageways to receive a first compressed section of the suture such that the first compressed section is compressed against the notch by the first compression section of the suture to substantially prevent motion of the suture through the passageways in a manner that permits the tissue retainer to move apart from the anchor.

22. A system for attaching a bone and a tissue together via a suture, the system comprising:
a suture; and
an anchor comprising:
a bone retention portion configured to engage the bone to attach the anchor to the bone; and
a suture retention portion attached to the bone retention portion, the suture retention portion comprising a plurality of passageways arranged to receive the suture, and a first notch;
wherein the suture is routed through the passageways such that a first anchor portion of the suture is able to be drawn through at least some of the passageways. substantially along only a first direction;
wherein the first anchor portion is further routed through the passageways such that a first compression section of the first anchor portion presses a compressed section of the first anchor portion against the first suture retention portion in response to tension urging the first anchor portion to move through the passageways opposite to the first direction.

23. The system of claim 22, wherein the bone retention portion comprises a threaded tip having a plurality of threads shaped to engage the bone to attach the anchor to the bone.

24. The system of claim 22, wherein the suture comprises first and second anchor portions, wherein the first anchor portion extends along a first pathway through the passageways and the second anchor portion extends along a second pathway through the passageways, wherein the first and second anchor portions under tension can only be advanced in a single direction along the first and second pathways, respectively.

25. The system of claim 24, wherein the first and second anchor portions are able to be independently drawn along the first and second pathways, respectively.

26. The system of claim 24, wherein the first anchor portion comprises the compression section and the compressed section, wherein the suture retention portion further comprises a second notch positioned to receive a compressed section of the second anchor portion such that the compressed section of the second anchor portion is compressed against the second notch by a compression section of the second anchor portion.

27. The system of claim 22, wherein the first notch is oriented substantially perpendicular to at least one passageway of the plurality of passageways.

28. A system for attaching a bone and a tissue together via a suture comprising first and second anchor portions, the system comprising:
a suture; and
an anchor comprising:
a bone retention portion configured to engage the bone to attach the anchor to the bone; and
a first suture retention portion attached to the bone retention portion, the first suture retention portion comprising a plurality of passageways arranged to define first and second pathways;
wherein the suture is routed through the passageways such that a first anchor portion of the suture is able to be drawn along the first pathway substantially along only a first direction and a second anchor portion of the suture is able to be drawn along the second pathway substantially only along a second direction independently of advancement of the first anchor portion along the first pathway;
wherein the first anchor portion is routed along the first pathway such that a first compression section of the first anchor portion presses another part of the first anchor portion against the first suture retention portion in response to tension urging the first anchor portion to move along the first pathway opposite to the first direction.

29. The system of claim 28, wherein the passageways comprise a primary passageway, a first secondary passageway, and a second secondary passageway, wherein the first pathway passes through the primary passageway and the first secondary passageway, and the second pathway passes through the primary passageway and the second secondary passageway.

30. The system of claim 28, wherein the first and second pathways are substantially symmetrical to each other across a long axis of the anchor.

31. The system of claim 30, wherein the plurality of passageways comprises two passageways symmetrically displaced from each other across a long axis of the anchor.

32. The system of claim 28, further comprising a tissue retainer comprising a second suture retention portion configured to retain a retainer portion of the suture.

33. The system of claim 32, wherein the second suture retention portion comprises one or more passageways through which the retainer portion is relatively freely movable along a retainer pathway, along either direction.

34. A method for attaching a bone and a tissue together via a suture through the use of a system comprising an anchor and a tissue retainer, the method comprising:
retaining a first anchor portion of the suture with a first suture retention portion of the anchor;
retaining a retainer portion of the suture with a second suture retention portion of the tissue retainer; and
engaging the bone with a bone retention portion of the anchor to attach the anchor to the bone;
wherein one of retaining the first anchor portion and retaining the retainer portion comprises inserting the suture along a first pathway through a plurality of passageways of the corresponding suture retention portion of the first and second suture retention portions such that the suture is able to be drawn only along a direction that draws the anchor and the tissue retainer closer together;
wherein the suture is routed such that a first compression section of the first anchor portion presses another part of the first anchor portion against the first suture retention portion in response to tension urging anchor and the tissue retainer to move apart.

35. The method of claim 34, wherein the bone retention portion comprises a threaded tip, wherein engaging the bone comprises engaging the bone with a plurality of threads of the threaded tip in response to rotation of the anchor.

36. The method of claim 34, wherein the suture further comprises a second anchor portion, the method further comprising retaining the second anchor portion with the first suture retention portion.

37. The method of claim 36, wherein the first suture retention portion comprises the plurality of passageways, wherein retaining the second anchor portion comprises inserting the second anchor portion along a second pathway through the plurality of passageways such that the second anchor portion is able to be drawn only along a direction that draws the anchor and the tissue retainer closer together.

38. The method of claim 37, wherein the second suture retention portion comprises one or more passageways, the method further comprising inserting the retainer portion through the one or more passageways of the tissue retainer such that the retainer portion is relatively freely movable through the one or more passageways of the tissue retainer along either direction.

39. The method of claim 37, further comprising drawing one of the first and second anchor portions along the corresponding pathway of the first and second pathways independently of motion of the other of the first and second anchor portions.

40. The method of claim 37, wherein the passageways comprise a primary passageway, a first secondary passageway, and a second secondary passageway, wherein inserting the first anchor portion along the first pathway comprises moving the first anchor portion through the primary passageway and the first secondary passageway, wherein inserting the second anchor portion along the second pathway comprises moving the second anchor portion through the primary passageway and the second secondary passageway.

41. The method of claim 34, wherein at least one of the first suture retention portion and the second suture retention portion comprises a notch positioned adjacent to the passageways, wherein retaining the first anchor portion comprises receiving a first compressed section of the suture such that the first compressed section is compressed against the notch by the first compression section of the suture to substantially prevent motion of the suture through the passageways in a manner that permits the tissue retainer to move apart from the anchor.

42. The method of claim 34, further comprising positioning the tissue retainer to abut the tissue.

43. The method of claim 42, further comprising moving the first anchor portion along the pathway to draw the bone and the tissue closer together.

44. A method for coupling a suture to a bone through the use of an anchor, the method comprising:
inserting a suture along a first pathway through a plurality of passageways of a suture retention portion of the anchor, such that the suture under tension can only be advanced in a single direction along the first pathway, wherein the first anchor portion is routed such that a first compression section of the first anchor portion presses another part of the first anchor portion against the suture retention portion in response to tension urging the suture to move through the passageways opposite to the first direction; and
rotating the anchor about an axis to induce engagement the anchor with the bone, thereby attaching the anchor to the bone.

45. The method of claim 44, wherein the bone retention portion comprises a threaded tip having a plurality of threads, wherein inducing engagement of the anchor with the bone comprises engaging the bone with the threads in response to rotation of the anchor to attach the anchor to the bone.

46. The method of claim 45, wherein the threaded tip comprises a sharpened shape, the method further comprising:
positioning the threaded tip against the bone; and
pressing the tip against the bone along the axis to induce penetration of the bone by the threaded tip.

47. The method of claim 44, wherein the suture comprises first and second anchor portions, wherein inserting the suture along the first pathway comprises inserting the first anchor portion along the first pathway and inserting the second anchor portion along the second pathway such that the second anchor portion under tension can only be advanced in a single direction along the second pathway.

48. The method of claim 47, further comprising drawing one of the first and second anchor portions along the corresponding pathway of the first and second pathways independently of motion of the other of the first and second anchor portions.

49. The method of claim 47, wherein the passageways comprise a primary passageway, a first secondary passageway, and a second secondary passageway, wherein inserting the first anchor portion along the first pathway comprises inserting the first anchor portion through the primary passageway and the first secondary passageway, wherein inserting the second anchor portion along the second pathway comprises inserting the second anchor portion through the primary passageway and the second secondary passageway.

50. The method of claim 44, wherein the suture retention portion comprises a notch positioned adjacent to the passageways, wherein retaining the first anchor portion comprises receiving a first compressed section of the suture such that the first compressed section is compressed against the notch by the first compression section of the suture to substantially prevent motion of the suture through the passageways in a manner that permits the tissue retainer to move apart from the anchor.

51. A method for coupling a suture to a bone through the use of an anchor, the method comprising:
    inserting the suture through a plurality of passageways of a suture retention portion of the anchor;
    receiving a compressed section of the suture in a first notch of the suture retention portion such that the compressed section is compressed against the first notch by a compression section of the suture; and
    receiving a bone retention portion of the anchor in the bone to retain the anchor.

52. The method of claim 51, wherein the bone retention portion comprises a threaded tip having a plurality of threads, wherein receiving the bone retention portion of the anchor into the bone comprises engaging the bone with the threads to attach the anchor to the bone.

53. The system of claim 51, wherein the suture comprises first and second anchor portions, wherein inserting the suture through the plurality of passageways comprises inserting the first anchor portion along a first pathway through the passageways and inserting the second anchor portion along an second pathway through the passageways, such that the first and second anchor portions under tension can only be advanced in a single direction along the first and second pathways, respectively.

54. The method of claim 53, further comprising drawing one of the first and second anchor portions along the corresponding pathway of the first and second pathways independently of motion of the other of the first and second anchor portions.

55. The method of claim 53, wherein the first anchor portion comprises the compression section and the compressed section, wherein the suture retention portion further comprises a second notch, the method further comprising receiving a compressed section of the second anchor portion in the second notch such that the compressed section of the second anchor portion is compressed against the second notch by a compression section of the second anchor portion.

56. A method for coupling a suture to a bone through the use of an anchor, the suture comprising a first anchor portion and a second anchor portion, the method comprising:
    inserting the first and second anchor portions along first and second pathways, respectively, through a plurality of passageways of a suture retention portion of the anchor such that either of the first and second anchor portions under tension can only be advanced along the corresponding pathway in a single direction, wherein the first anchor portion is routed through the passageways such that a first compression section of the first anchor portion presses another part of the first anchor portion against the first suture retention portion in response to tension urging the first anchor portion to move through the passageways opposite to the single direction;
    receiving a bone retention portion of the anchor in the bone to retain the anchor; and
    further advancing only one of the first and second anchor portions along the corresponding pathway.

57. The method of claim 56, wherein the passageways comprise a primary passageway, a first secondary passageway, and a second secondary passageway, wherein inserting the first and second anchor portions along the first and second pathways comprises inserting the first anchor portion through the primary passageway and the first secondary passageway, and inserting the second anchor portion through the primary passageway and the second secondary passageway.

58. The method of claim 56, wherein inserting the first and second anchor portions along the first and second pathways comprises positioning the first and second anchor portions substantially symmetrically to each other across a long axis of the anchor.

59. The method of claim 56, further comprising inserting a retainer portion of the suture through one or more passageways of a tissue retainer such that advancing only one of the first and second anchor portions along the corresponding pathway draws the tissue retainer closer to the anchor.

60. The method of claim 56, wherein the second anchor portion is routed through the passageways such that a second compression section of the second anchor portion presses another part of the second anchor portion against the first suture retention portion in response to tension urging the second anchor portion to move through the passageways opposite to the single direction.

* * * * *